United States Patent [19]
Julius et al.

[11] Patent Number: 6,093,693
[45] Date of Patent: *Jul. 25, 2000

[54] B CELL ACTIVATION

[75] Inventors: Michael H. Julius; Dominik Filipp, both of Toronto; Kamel Alizadeh-Khiavi, London, all of Canada

[73] Assignee: The Wellesley Hospital Foundation, Toronto, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/746,883

[22] Filed: Nov. 18, 1996

[51] Int. Cl.$^7$ .......................... A61K 38/18; C07K 14/475
[52] U.S. Cl. ............................. 514/8; 514/21; 424/185.1; 424/278.1; 530/351
[58] Field of Search .............................. 424/185.1, 198.1, 424/278.1; 514/12, 8, 21; 530/351

[56] References Cited

U.S. PATENT DOCUMENTS 5,543,303  8/1996  Goyert .

FOREIGN PATENT DOCUMENTS 9319772  10/1993  WIPO .
9632418  10/1996  WIPO .

OTHER PUBLICATIONS

Löms, Ziegler–Heitbrock, H.W. et al., European Journal of Immunology, 24(8):1937–1940 1994, "CD14 is expressed and functional in human B cells."

Ulevitch, R.J. et al., Annual Review of Immunology, 13:437–457, 1995, "Receptor–dependent mechanisms of cell stimulation by bacterial endotoxin."

Yang et al. "Analysis of the CD14 receptor associated with bovine alveolar macrophages", Inflammation, 20(1):97–106, XP002062355, Feb. 1996.

Setoguchi et al., "Mouse and human CD14 (myeloid cell–specific leucin rich glycoprotein) primary structure deduced from cDNA clones", Biochimica et Biophysica ACTA, 1008(2):213–222, XP002062356 (1989).

Jabara et al. "Engagement of CD14 on monocytes inhibits the synthesis of human Igs., including IgE", The Journal of Immunology, 153:972–978, XP002062357 (1994).

Ikeda et al., "Molecular cloning of bovine CD14 gene", J. Vet. Med. Sci., 59(8):715–719, XP002062359 (1997).

Wang, et al., "Detection and identification of soluble CD14 in bovine milk", Molecular Biology of the Cell, 8(5):85a, XP002062360, Nov. 1997.

Yang et al., "Soluble CD14 lipopolysaccharide–binding protein from bovine serum enable bacterial lipopolysaccharide–mediated cytotoxicity and activation of . . . ", Journal of Leukocyte Biology, 59(2):241–247, XP002062361, Feb. 1996.

Simmons et al., "Monocyte antigen CD14 is a phospholipid anchored membrane protein" Blood, 73(1):284–289, XP002062358, Jan. 1989.

Juan, Todd S.–C, et al., The Journal of Biological Chemistry, 270:1382–1387, 1995, "Soluble CD14 truncated at amino acid 152 binds lipopolysaccharide (LPS) and enables cellular responses to LPS".

Viriyakosal, S. and T.H. Kirkland, Infection and Immunity 64:653–656, 1996. "The N–terminal half of membrane CD14 is a functional cellular lipopolysaccharide receptor".

"A Colostral Protein that Induces the Growth and Differentiation of Resting B Lymphocytes". M.H. Julius et al., The Journal of Immunology, vol. 140, pp. 1366–1371, No. 5, Mar. 1, 1987.

*Primary Examiner*—Christina Y. Chan
*Assistant Examiner*—Mary Beth Tung
*Attorney, Agent, or Firm*—John C. Hunt

[57] ABSTRACT

A novel protein purified from bovine colostral whey and isolated nucleotide sequences encoding the protein. The isolated bovine protein has homology with human CD14 and murine CD14 and so is referred to as bovine CD14. A method of activating B cells, and particularly of activating B cells in a mammal, such as a human, in need of such activation by administering CD14 is described. CD14 can be incorporated into infant formula. CD14 can be administered to an infant, as by feeding to the infant such formula. CD14 can be incorporated as part of a vaccination. CD14 can be administered to a patient having a T cell immune deficiency, for example, a particular T cell dysfunction in which gp39 is under expressed on or totally absent from the cell surface of patient T cells. Preparation of medicaments including CD14 for activating B cells in a mammal in need of such activation is described. Natural or recombinant CD14 can be used.

4 Claims, 19 Drawing Sheets

Purification of Bovine LAIT-Protein

Figure 2

Sequence Homology Among Bo-LAIT Fragments and Human CD14

```
1
MERASCLLLL LLPLVHVSAT TPEPCELDDE DFRCVCNFSE PQPDWSEAFQ
                   D  -?--?--NN? ??-?-?

S1
CVSAVEVEIH AGGENCEPFL KRVDADADPR QYADTVKALR VRRLTVGAAQ
  V----?-S ---LSL?

101
VPAQLLVGAL RVLAYSRLKE LTLEDLKITG TMPPLPLEAT GLALSSLRLR

1S1
NVSWATGRSW LAELQQWLKP GLKVLSIAQA HSPAFSYEQV RAFPALTSLD
?---T--GA? -G---

201
LSDNPGLGER GLMAALCPHK FPAIQNLALR NTGMETPTGV CAALAAAGVQ
                                      ---S-P A-----LR--

2S1
PHSLDLSHNS LRATVNPSAP RCMWSSALNS LNLSFAGLEQ VPKGLPAKLR
-Q-------? -?V?

301
VLDLSCNRLN RAPQPDELPE VDNLTLDGNP FLVPGTALPH EGSMNSGVVP
                                                  L----V

3S1
ACARSTLSVG VSGTLVLLQG ARGFA
???--
```

Affinity Purification of Bovine and Human
Colostral LAIT-Protein

Heat Lability and Antibody Mediated Inhibition of Bo-LAIT Activity

Characterization of the Bovine CD14 Locus

Nucleic Acid Sequence Comparison of Bovine, Human, and Mouse CD14 cDNAs

```
Majority        A T G G A G C G C G T G C C C T G C T T G T T G C T G C T G C T G
                          10                  20                  30

Bovine CD14 cDNA  A T G G T G T G C G T G C C C T A C C T G C T G C T G C T G C T G  33
Human  CD14 cDNA  A T G G A G C G C G C G T C C T G C T T G C T G C T G C T G     33
Mouse  CD14 cDNA  A T G G A G C G T G T G C T T G G C T T G T T G C T G T T G C T T  33

Majority        C T G C C G - - - C T G G T G C A C G T C T C T G C G G C C A C A
                          40                  50                  60

Bovine CD14 cDNA  C T G C C G T C A C T G C T G C G T G T G T C T G C G G A C A C A  66
Human  CD14 cDNA  C T G C C G - - - C T G G T G C A C G T C T C T G C G A C C A C G  63
Mouse  CD14 cDNA  C T G - - - - - - - - - G T G C A C G C C T C T C C C G C C C A  57

Majority        C C A G A A C C C T G C G A G C T G G A C G A X G A A G A T T T C
                          70                  80                  90

Bovine CD14 cDNA  A C A G A A C C C T G C G A G C T G G A C G A C G A C G A T T T C  99
Human  CD14 cDNA  C C A G A A C C T T G T G A G C T G G A C G A T G A A G A T T T C  96
Mouse  CD14 cDNA  C C A G A G C C C T G C G A G C T A G A C G A G G A A A - - - - -  86

Majority        C G T T G T G T C T G C A A C T T C T C X G A T C C G A A G C C X
                         100                 110                 120                 130

Bovine CD14 cDNA  C G T T G T G T C T G C A A C T T C A C G G A T C C G A A G C C T  132
Human  CD14 cDNA  C G C T G C G T C T G C A A C T T C T C C G A A C C T C A G C C C  129
Mouse  CD14 cDNA  - G T T G T T C C T G C A A C T T C T C A G A T C C G A A G C C A  117

Majority        G A C T G G T C C A G C G C C T T C C A G T G T X T G G X T G C X
                         140                 150                 160

Bovine CD14 cDNA  G A C T G G T C T A G C G C C G T T C A G T G T A T G G T T G C C  165
Human  CD14 cDNA  G A C T G G T C C G A A G C C T T C C A G T G T G T G T C T G C A  162
Mouse  CD14 cDNA  G A T T G G T C C A G C G C T T T C A A T T G T T T G G G G G C G  150

Majority        G T A G A G G T G G A G A T C X A T G C C G G C G G C C G C A G C
                         170                 180                 190

Bovine CD14 cDNA  G T C G A G G T G G A G A T C A G T G C C G G C G G C C G C A G C  198
Human  CD14 cDNA  G T A G A G G T G G A G A T C C A T G C C G G C G G T C T C A A C  195
Mouse  CD14 cDNA  G C A G A T G T G G A A T T G T A C G G C G G C G G C C G C A G C  183

Majority        C T G G A A C A G T T T C T A A A G C G X G T C G A X X C G G A C
                         200                 210                 220                 230

Bovine CD14 cDNA  C T G G A A C A G T T T C T C A A G G G A G C C G A - - - - - - C  225
Human  CD14 cDNA  C T A G A G C C G T T T C T A A A G C G C G T C G A T G C G G A C  228
Mouse  CD14 cDNA  C T G G A A T A C C T T C T A A A G C G T G T G G A C A C G G A A  216
```

FIG. 6 A

Nucleic Acid Sequence Comparison of Bovine,
Human, and Mouse CD14 cDNAs

```
Majority          G C C G A C C C G X G G C A G T A T G C T G A C A C X A T C A A G
                                  240             250             260
Bovine CD14 cDNA  A C C A A C C C G A A G C A G T A T G C T G A C A C A A T C A A G  258
Human  CD14 cDNA  G C C G A C C C G C G G C A G T A T G C T G A C A C G G T C A A G  261
Mouse  CD14 cDNA  G C A G A T C T G G G G C A G T T C A C T G A T A T T A T C A A G  249

Majority          G C T C T G C G C G T X C G G C G G C T C A C G G T G G G X G C C
                                  270             280             290
Bovine CD14 cDNA  G C T C T G C G C G T T C G G C G A C T C A A G C T G G G C G C T  291
Human  CD14 cDNA  G C T C T C C G C G T G C G G C G G C T C A C A G T G G G A G C C  294
Mouse  CD14 cDNA  T C T C T G T C C T T A A A G C G G C T T A C G G T G C G G C C    282

Majority          G C A C A G G T T C C T G C T C A G C T T C T G G T C G G C G C C
                          300             310             320             330
Bovine CD14 cDNA  G C A C A G G T T C C T G C T C A G C T T C T G G T C G C C G T T  324
Human  CD14 cDNA  G C A C A G G T T C C T G C T C A G C T A C T G G T A G G C G C C  327
Mouse  CD14 cDNA  G C G C G G A T T C C T A G T C G G A T T C T A T T C G G A G C C  315

Majority          C T G C G T G T G C T C G G G T A C T C C C G C C T C A A G G A A
                                  340             350             360
Bovine CD14 cDNA  C T G C G C G C G C T C G G G T A C T C T C G T C T C A A G G A A  357
Human  CD14 cDNA  C T G C G T G T G C T A G C G T A C T C C C G C C T C A A G G A A  360
Mouse  CD14 cDNA  C T G C G T G T G C T C G G G A T T T C C G G C C T C C A G G A A  348

Majority          C T G A C G C T T G A G G A C C T X G A G G T A A C C G G C A C C
                                  370             380             390
Bovine CD14 cDNA  C T G A C G C T T G A G G A C C T G G A G G T A A C C G G C C C A  390
Human  CD14 cDNA  C T G A C G C T C G A G G A C C T A A A G A T A A C C G G C A C C  393
Mouse  CD14 cDNA  C T G A C T C T T G A A A A T C T C G A G G T A A C C G G C A C C  381

Majority          A C G C C X C C G C C G C C T C T G G A A G C C A C X G G A C C T
                                  400             410             420
Bovine CD14 cDNA  A C G C C C C C G A C G C C T C T G G A A G C C G C T G G G C C T  423
Human  CD14 cDNA  A T G C C T C C G C T G C C T C T G G A A G C C A C A G G A C T T  426
Mouse  CD14 cDNA  G C G C C G C C A C C G C T T C T G G A A G C C A C C G G A C C C  414

Majority          G C X C T C A C C A X C T T G A G C C T X C G C A A C G T G T C G
                          430             440             450             460
Bovine CD14 cDNA  G C G C T C A C C A C C C T C A G T C T G C G T A A C G T A T C G  456
Human  CD14 cDNA  G C A C T T T C C A G C T T G C G C C T A C G C A A C G T G T C G  459
Mouse  CD14 cDNA  G A T C T C A A C A T C T T G A A C C T C C G C A A C G T G T C G  447
```

FIG. 6 B

Nucleic Acid Sequence Comparison of Bovine, Human, and Mouse CD14 cDNAs

| | Sequence | |
|---|---|---|
| Majority | TGGGCAACAGGGGGTGCCTGGCTCGCCGAACTG | |
| Bovine CD14 cDNA | TGGACAACAGGAGGTGCCTGGCTCGGCGAACTG | 489 |
| Human CD14 cDNA | TGGGCGACAGGGCGTTCTTGGCTCGCCGAGCTG | 492 |
| Mouse CD14 cDNA | TGGGCAACAAGGGATGCCTGGCTCGCAGAACTG | 480 |
| Majority | CAGCAGTGGCTCAAGCCTGGXCTCAAGGTACTG | |
| Bovine CD14 cDNA | CAGCAGTGGCTCAAGCCTGGGCTCAGGGTGCTG | 522 |
| Human CD14 cDNA | CAGCAGTGGCTCAAGCCAGGCCTCAAGGTACTG | 525 |
| Mouse CD14 cDNA | CAGCAGTGGCTAAAGCCTGGACTCAAGGTACTG | 513 |
| Majority | AGCATTGCCCAAGCACACTCGCTTGCCTTTTCC | |
| Bovine CD14 cDNA | AACATTGCCCAAGCACACTCGCTTGCCTTTCCG | 555 |
| Human CD14 cDNA | AGCATTGCCCAAGCACACTCGCCTGCCTTTTCC | 558 |
| Mouse CD14 cDNA | AGTATTGCCCAAGCACACTCACTCAACTTTTCC | 546 |
| Majority | TGCGAACAGGTCCGCGCCTTCCCGGCCCTCACC | |
| Bovine CD14 cDNA | TGCGCAGGGCTCTCCACCTTCGAGGCGCTCACC | 588 |
| Human CD14 cDNA | TGCGAACAGGTTCGCGCCTTCCCGGCCCTTACC | 591 |
| Mouse CD14 cDNA | TGCGAACAGGTCCGCGTCTTCCCTGCCCTCTCC | 579 |
| Majority | ACCCTAGACCTGTCTGACAATCCTGGACTGGGC | |
| Bovine CD14 cDNA | ACCCTAGACCTGTCTGACAATCCAGTCTCGGC | 621 |
| Human CD14 cDNA | AGCCTAGACCTGTCTGACAATCCTGGACTGGGC | 624 |
| Mouse CD14 cDNA | ACCTTAGACCTGTCTGACAATCCTGAATTGGGC | 612 |
| Majority | GAXACGXGGACTGATGGCAGCTCTCTGTCCCCA | |
| Bovine CD14 cDNA | GACACG-GGGCTGATGGCAGCTCTCTGTCCGAA | 653 |
| Human CD14 cDNA | GA-ACGCGGACTGATGGCGGCTCTCTGTCCCCA | 656 |
| Mouse CD14 cDNA | GAGA-GAGGACTGATCTCAGCCCTCTCTGTCCCCT | 644 |
| Majority | CAAGTTCCCGGCCCTCCAAXATCTAGCGCTGCG | |
| Bovine CD14 cDNA | CAAGTTCCCGGCCCTCCAATATCTAGCGCTACG | 686 |
| Human CD14 cDNA | CAAGTTCCCGGCCATCCAGAATCTAGCGCTGCG | 689 |
| Mouse CD14 cDNA | CAAGTTCCCGACCCTCCAAGTTTTAGCGCTGCG | 677 |

FIG. 6 C

Nucleic Acid Sequence Comparison of Bovine, Human, and Mouse CD14 cDNAs

| | | |
|---|---|---|
| Majority | CAACGCGGGGATGGAGACGCCCAGCGGCGTGTG | |
| | 700          710          720 | |
| Bovine CD14 cDNA | CAACGCGGGGATGGAGACGCCGAGCGGCGTGTG | 719 |
| Human CD14 cDNA | CAACACAGGAATGGAGACGCCCACAGGCGTGTG | 722 |
| Mouse CD14 cDNA | TAACGCGGGGATGGAGACGCCCAGCGGCGTGTG | 710 |
| Majority | CGCXGCGCTGGCGGCAGCAAGGGTGCAGCCCCA | |
| | 730          740          750 | |
| Bovine CD14 cDNA | CGCGGCGCTGGCGGCAGCGAGGGTGCAGCCCCA | 752 |
| Human CD14 cDNA | CGCCGCACTGGCGGCGGCAGGTGTGCAGCCCCA | 755 |
| Mouse CD14 cDNA | CTCTGCGCTGGCCGCAGCAAGGGTACAGCTGCA | 743 |
| Majority | AAGCCTAGACCTCAGCCACAACTCGCTGCGCGX | |
| | 760       770       780       790 | |
| Bovine CD14 cDNA | AAGCCTGGACCTCAGCCACAACTCGCTGCGCGT | 785 |
| Human CD14 cDNA | CAGCCTAGACCTCAGCCACAACTCGCTGCGCGC | 788 |
| Mouse CD14 cDNA | AGGACTAGACCTTAGTCACAATTCACTGCGGGA | 776 |
| Majority | CACCGCA--CCCXGGCGCTCCGAGATGTGTCTG | |
| | 800         810         820 | |
| Bovine CD14 cDNA | CACCGC---CCCGGGTGCTACCCGATGTGTCTG | 815 |
| Human CD14 cDNA | CACCGTAAACCCTAGCGCTCCGAGATGCATGTG | 821 |
| Mouse CD14 cDNA | TGCTGCA------GGCGCTCCGAGTTGTGACTG | 803 |
| Majority | GCCCAGTGCXCTAAACTCXCTCAATCTGTCGTT | |
| | 830         840         850 | |
| Bovine CD14 cDNA | GCCCAGTGCACTAAGGTCTCTCAATTTGTCGTT | 848 |
| Human CD14 cDNA | GTCCAGCGCCCTGAACTCCCTCAATCTGTCGTT | 854 |
| Mouse CD14 cDNA | GCCCAGTCAGCTAAACTCGCTCAATCTGTCTTT | 836 |
| Majority | CGCTGGGCTGGAGCAGGTGCCTAAAGGACTGCC | |
| | 860         870       880       890 | |
| Bovine CD14 cDNA | CGCTGGGCTGGAGCAAGTGCCTAAGGGACTGCC | 881 |
| Human CD14 cDNA | CGCTGGGCTGGAACAGGTGCCTAAAGGACTGCC | 887 |
| Mouse CD14 cDNA | CACTGGGCTGAAGCAGGTACCTAAAGGGCTGCC | 869 |
| Majority | AGCCAAGCTCAGCGTGCTXGATCTCAGCTGCAA | |
| | 900         910         920 | |
| Bovine CD14 cDNA | CCCTAAGCTCAGCGTGCTTGATCTCAGCTGCAA | 914 |
| Human CD14 cDNA | AGCCAAGCTCAGAGTGCTCGATCTCAGCTGCAA | 920 |
| Mouse CD14 cDNA | AGCCAAGCTCAGCGTGCTGGATCTCAGTTACAA | 902 |

FIG. 6 D

Nucleic Acid Sequence Comparison of Bovine, Human, and Mouse CD14 cDNAs

```
Majority           CAGGCTGAACAGGGAGCCGCGGCCAGACGAGCT
                         930         940         950

Bovine CD14 cDNA   CAAGCTAAGCAGGGAGCCGCGGCGAGACGAGCT   947
Human  CD14 cDNA   CAGACTGAACAGGGCGCCGCAGCCTGACGAGCT   953
Mouse  CD14 cDNA   CAGGCTGGATAGGAACCTAGCCCAGATGAGCT    935

Majority           GCCCGAGGTGGATAACCTGACACTGGACGGAAA
                         960         970         980         990

Bovine CD14 cDNA   GCCCGAGGTAAATGACCTGACTCTGGACGGAAA   980
Human  CD14 cDNA   GCCCGAGGTGGATAACCTGACACTGGACGGGAA   986
Mouse  CD14 cDNA   GCCCCAAGTGGGGAACCTGTCACTTAAAGGAAA   968

Majority           TCCCTTTCTGGACCCTGGAXCXXTCCXXCXCCA
                         1000        1010        1020

Bovine CD14 cDNA   TCCCTTTCTGGACCCTGGAGCCCTCCAGCACCA   1013
Human  CD14 cDNA   TCCCTTCCTGGTCCCTGGAACTGCCCTCCCCCA   1019
Mouse  CD14 cDNA   TCCCTTTTTGGACTCTGAA----TCCCAC-TCG   996

Majority           XAAXGGCTCAATGAXCTCCGGCGTGGTCCCAGC
                         1030        1040        1050

Bovine CD14 cDNA   AAATGACCCGATGATCTCCGGCGTGGTCCCAGC   1046
Human  CD14 cDNA   CGAGGGCTCAATGAACTCCGGCGTGGTCCCAGC   1052
Mouse  CD14 cDNA   GAGAAGTTTAA----CTCTGGCGTAGTCACCGC   1025

Majority           CTGTGCXCGTTCXXXCCCTGXCXGTGGGGGTGTC
                         1060        1070        1080

Bovine CD14 cDNA   CTGTGCGCGTTCTGCCTTGACCATGGGGGTGTC   1079
Human  CD14 cDNA   CTGTGCACGTTCGACCCTGTCGGTGGGGGTGTC   1085
Mouse  CD14 cDNA   CGGAGCTCCATCATCCCAAGCAGTGGCCTTGTC   1058

Majority           AGGAACCCTGGCGCTGCTCCAAGGAGCCCGXGG
                         1090        1100        1110        1120

Bovine CD14 cDNA   AGGAGCCCTGGCGCTGCTTCAAGGAGCCCGAGG   1112
Human  CD14 cDNA   GGGAACCCTGGTGCTGCTCCAAGGGGCCCGGGG   1118
Mouse  CD14 cDNA   AGGAACTCTGGCTTTGCTCCTAGGAGATCGCCT   1091

Majority           CTTTGCXTAA
                         1130

Bovine CD14 cDNA   CTTCGCGTAA   1122
Human  CD14 cDNA   CTTTGCCTAA   1128
Mouse  CD14 cDNA   CTTTGTTTAA   1101
```

FIG. 6 E

Amino Acid Sequence Comparison of Bovine, Human, and Mouse CD14

```
Majority      MERVXXLLLLLLP-LVHVSAXTPEPCELDDEDFRC
                      10        20        30
Bovine CD14   MVCVPYLLLLLLPSLLRVSADTTEPCELDDDDFRC  35
Human  CD14   MERASCLLLLLLP-LVHVSATTPEPCELDDEDFRC  34
Mouse  CD14   MERVLGLLLLLL---VHASPAPPEPCELDEES--C  30

Majority      VCNFSDPKPDWSSAFQCXXAVEVEIXAGGRSLEXF
                      40        50        60        70
Bovine CD14   VCNFTDPKPDWSSAVQCMVAVEVEISAGGRSLEQF  70
Human  CD14   VCNFSEPQPDWSEAFQCVSAVEVEIHAGGLNLEPF  69
Mouse  CD14   SCNFSDPKPDWSSAFNCLGAADVELYGGRSLEYL  65

Majority      LKRVDADADPXQYADTIKALRVRRLTVGAAQVPAQ
                      80        90        100
Bovine CD14   LK--GADTNPKQYADTIKALRVRRLKLGAAQVPAQ  103
Human  CD14   LKRVDADADPRQYADTVKALRVRRLTVGAAQVPAQ  104
Mouse  CD14   LKRVDTEADLGQFTDIIKSLSLKRLTVRAARIPSR  100

Majority      LLVGALRVLGYSRLKELTLEDLEVTGTXPPXPLEA
                      110       120       130       140
Bovine CD14   LLVAVLRALGYSRLKELTLEDLEVTGPTPPTPLEA  138
Human  CD14   LLVGALRVLAYSRLKELTLEDLKITGMPPLPLEA   139
Mouse  CD14   ILFGALRVLGISGLQELTLENLEVTGAPPPLLEA   135

Majority      TGPALXXLXLRNVSWATGXAWLAELQQWLKPGLKV
                      150       160       170
Bovine CD14   AGPALTTLSLRNVSWTTGGAWLGELQQWLKPGLRV  173
Human  CD14   TGLALSSLRLRNVSWATGRSWLAELQQWLKPGLKV  174
Mouse  CD14   TGPDLNILNLRNVSWATRDAWLAELQQWLKPGLKV  170

Majority      LSIAQAHSLAFSCEQVRXFPALTTLDLSDNPXLGE
                      180       190       200       210
Bovine CD14   LNIAQAHSLAFPCAGLSTFEALTTLDLSDNPSLGD  208
Human  CD14   LSIAQAHSPAFSYEQVRAFPALTSLDLSDNPGLGE  209
Mouse  CD14   LSIAQAHSLNFSCEQVRVFPALSTLDLSDNPELGE  205

Majority      RGLMAALCPXKFPALQXLALRNAGMETPSGVCAAL
                      220       230       240
Bovine CD14   TGLMAALCPNKFPALQYLALRNAGMETPSGVCAAL  243
Human  CD14   RGLMAALCPHKFPAIQNLALRNTGMETPTGVCAAL  244
Mouse  CD14   RGLISALCPLKFPTLQVLALRNAGMETPSGVCSAL  240
```

FIG. 7 A

Amino Acid Sequence Comparison of Bovine, Human, and Mouse CD14

```
Majority     AAARVQPQSLDLSHNSLRXT-APGAPRCXWPSALN
                   250         260         270         280
Bovine CD14  AAARVQPQSLDLSHNSLRVT-APGATRCVWPSALR  277
Human  CD14  AAAGVQPHSLDLSHNSLRATVNPSAPRCMWSSALN  279
Mouse  CD14  AAARVQLQGLDLSHNSLRDA-A-GAPSCDWPSQLN   273

Majority     SLNLSFAGLEQVPKGLPAKLSVLDLSCNRLXRXPX
                      290         300         310
Bovine CD14  SLNLSFAGLEQVPKGLPPKLSVLDLSCNKLSREPR  312
Human  CD14  SLNLSFAGLEQVPKGLPAKLRVLDLSCNRLNRAPQ  314
Mouse  CD14  SLNLSFTGLKQVPKGLPAKLSVLDLSYNRLDRNPS   308

Majority     PDELPEVXNLTLDGNPFLDPGXXXXHXXXMNSGVV
                   320         330         340         350
Bovine CD14  RDELPEVNDLTLDGNPFLDPGALQHNDPMISGVV   347
Human  CD14  PDELPEVDNLTLDGNPFLVPGTALPHEGSMNSGVV  349
Mouse  CD14  PDELPQVGNLSLKGNPFLD---SESHSEKFNSGVV  340

Majority     PACARSXLXVGVSGTLALLQGARGFA
                      360         370
Bovine CD14  PACARSALTMGVSGALALLQGARGFA          373
Human  CD14  PACARSTLSVGVSGTLVLLQGARGFA          375
Mouse  CD14  TAGAPSSQAVALSGTLALLLGDRLFV          366
```

FIG. 7 B

Primer Design for the Amplification of Bovine
CD14 Coding Region

Figure 8 A

Baculovirus expression system

Forward 5'- GCT AGC GCT AGC CAC CAT GGT GTG CGT GCC CTA CCT GCT - 3'

Reverse 5' - GCT AGC GCT AGC CGC GAA GCC TCG GGC TCC TTG AAG - 3'

Figure 8 B

Mammalian expression system

Forward 5' - CTC GAG CTC GAG GCT AGC CAC CAT GGT GTG CGT GCC - 3'

Reverse 5' - CTC GAGCTGAG GGA TCC CTA AGC GTA ATC TGG AAC - 3'

Immunoblotting of Native and Recombinant Bovine CD14

Differentiation Promoting Activity of nBo-LAIT

Comparative Growth Promoting Activities of nBo- and rBo- LAIT Protein

Growth Promoting Activity of nBo-LAIT
on Human Cord and Tonsil B Cells

B CELL ACTIVATION

FIELD OF INVENTION

This invention relates to proteins that activate B cells.

Bone marrow-derived "B" lymphocytes, commonly called B cells, are a type of white blood cell present in the lymph, the blood, and in secondary lymphoid organs of the immune system. B cells are the precursors of antibody secreting cells, plasma cells, and as such are central to the induction of humoral immune responses.

The induction of most humoral immune responses in the adult involves a number of cellular interactions among thymus-derived T lymphocytes, commonly called T cells, antigen presenting cells (APC), and B cells [J. Exp. Med 147:1159, 1978; PNAS 77:1612,1982; PNAS 79:1989, 1982; Immunol. Rev. 95:914,1987].

As currently understood, T cell-dependent B cell activation involves activation of T cells upon their recognition of antigen, as presented by APC in conjunction with proteins encoded within the major histocompatibility complex (MHC), which are expressed on the cell surface of the APC. This antigen specific and MHC restricted T cell-APC interaction results in reciprocal activation of the two cell types, and the alteration of T cell physiology such that "helper function" becomes manifest.

Helper T cells can activate antigen specific B cells. Antigen specificity of the T cell-B cell interaction is maintained as a consequence of the ultimate capacity of the B cell to function as an APC. Thus, while resting, quiescent B cells are not efficient APC (PNAS 79 1989, 1982), they specifically interact with antigen through membrane associated immunoglobulin, the specificity of which reflects that of the immunoglobulin their daughter cells will secrete (J. Exp. Med. 140:904, 1974). Immunoglobulin mediated internalization of antigen by the specific B cell, which may involve presentation by yet another sort of APC, the follicular dendritic cell, results in the initiation of antigen processing by the B cell, the up-regulation of MHC Class II and B7 expression, and the presentation of antigen derived peptides in the context of MHC (J. Exp. Med. 178: 2055, 1993). The B cell activated by this route is a target for the activated helper T cell.

T cell helper function includes signals delivered through both T-B cell contact, and the interaction of T cell derived soluble mediators, referred to as cytokines, with their cognate ligands expressed on the B call plasma membrane. T cell-B cell contact is also MHC restricted, analogous to the T cell-APC interaction (Eur. J. Immunol. 12:627,1982; Eur. J. Immunol. 12:634,1982). However, the specific interaction of the molecules which mediate the MHC restricted interaction between the two lymphocyte lineages, specifically, the T cell receptor for antigen (TcR), and the MHC/antigen complex expressed by the B cells, do not predicate the induction of B cell growth and differentiation (Eur. J. Immnunol. 18:375, 1988).

The essential molecular interaction, reflected by the requirement for T cell-B cell contact, is mediated by CD40 expressed on the plasma membrane of the B cell, and its cognate ligand, gp39 (or CD40L), expressed on the plasma membrane of the T cell (PNAS 89:6550, 1992; Nature 357:80, 1992). Consistent with this paradigm is the observation that membrane expression of the latter increases upon T-APC interaction, as well as subsequent to T cell-B cell interaction (PNAS 89:6550, 1992). Further, membrane immunoglobulin mediated B cell interaction with antigen results in the increased membrane expression of CD40 (Sem. in Immunol 6:303, 1994). The interaction between CD40 and CD40L predicates the induction of B cell growth, B cell differentiation into immunoglobulin secreting cells, and immunoglobulin isotype switching (J. Exp. Med. 178:1567, 1993).

Consistent with this model is the observation that soluble CD40L, or monoclonal antibody (mAb) specific for CD40 can induce B cell growth and differentiation to immunoglobulin secretion (Sem. in Immunol. 6:267, 1994; PNAS 83:4494, 1986; J. Immunol. 140:1425, 1988).

In addition to the obligate requirement for T cell-B cell contact, a number of T cell derived cytokines, IL-2, IL-4 and IL-5 are central to B call growth and differentiation. B cell susceptibility to these cytokines is for the most part limited by prior contact with a T cell. Thus, subsequent to T cell contact, the B cells increase expression of cytokine specific membrane receptors (PNAS 80:6628, 1983; J. Immunol. 145:2025, 1990; J. Immunol. 146;1118, 1991). IL-2 and IL-5 have been demonstrated to support the growth of activated B cells (PNAS 77:1612, 1980; Immunol. Rev. 52; 115, 1980) Further, IL-4 and anti-immunoglobulin have been shown to synergize in supporting B cell growth (J. Exp. Med. 155:914, 1982).

Notable exceptions in this context are the quiescent B cell responses to IL-4 and IL-5. IL-4 induces the de novo transcription and translation of MHC Class II proteins (J. Exp. Med. 155:914, 1982; PNAS 81:6149, 1984; J. Exp. Med. 160;679, 1984), and IL-5 is able to support the differentiation of quiescent B cells to high rate immunoglobulin secretion in the absence of cell growth (Eur. J. Immunol. 22:2323,1992).

In any event, signals derived from molecular interactions amongst membrane molecules on T cells and B cells, and from those of T cell derived cytokines interacting with their cognate receptors on B cells are parts of a complex signaling system. Each signal drives the B cell to another stage of activation, rendering it susceptible to subsequent progression signals. These signals complement one another, rather than having the capacity, individually, to drive the complete process of B cell growth and differentiation (Immunol. Rev. 95:177, 1987)

In 1988, a unique activity in ovine colostrum was discovered (J. Immunol. 140:1366, 1988). Proline Rich Protein (PRP) had been partially purified using classical techniques of protein purification. This material was shown to support the induction of quiescent B cells into cell cycle, and to support their differentiation into high rate immunoglobulin secreting cells. This was apparently the first report of a protein of mammalian origin that mediates these functions.

A monoclonal antibody specific for ovine PRP was subsequently prepared. When PRP preparations were passed over an affinity column prepared using the antibody, all of the PRP was retained by the column, as assessed by Western blotting analysis of eluate and effluent. However, all of the B cell stimulatory activity was found in the effluent. Thus, the published characterization of the B cell tropic bioactivity present in ovine colostrum was not attributable to PRP (unpublished information).

This invention features a novel protein purified from bovine colostral whey and isolated nucleotide sequences encoding the protein. The isolated bovine protein has homology with human CD14 and murine CD14 and so is referred to as bovine CD14. The invention includes a method of activating B cells, and particularly of activating B cells in a mammal in need of such activation by administering CD14.

In a preferred embodiment, the mammal is a human patient.

According to one aspect, the invention includes incorporating CD14 into infant formula. The invention includes administering CD14 to an infant, a preferred mode of administration being feeding to the infant such formula.

In another aspect, the invention includes incorporating CD14 as part of a vaccination. The invention includes administering CD14 and antigen to a patient in need of immunization, a preferred mode of administration including administering a single preparation containing both CD14 and the antigen.

In another aspect, the invention includes administering CD14 to a patient having a T cell immune deficiency. In a preferred aspect, the invention includes administering CD14 to a patient suffering from a particular T cell dysfunction in which gp39 is under expressed on or totally absent from the cell surface of patient T cells.

The invention includes use of CD14 in preparation of medicaments for activating B cells in a mammal in need of such activation.

Natural or recombinant CD14 can be used in the invention. In addition, biologically active fragments of CD14 having the ability to activate B cells are included.

In the context of this invention, the term "CD14" includes murine, bovine or human CD14.

BRIEF DESCRIPTION OF THE DRAWINGS

FIG. 1A shows an anion exchange [FPLC MONO Q, Pharmacia] chromatogram (Absorbance at about 280 nm) of 50 mg of 62% $(NH_4)_2SO_4$ using a gradient of 50–400 mM NaCl in 10 mM Bis-tris propane, with a simultaneous pH gradient of 7.5 to 9.5. Table 1A indicates the bioactivity of the fraction with peak activity, fraction #57. High buoyant density mouse splenic B cells were isolated as previously described (J. Immunol. 131:581, 1983), and cultured at $5 \times 10^4$ cells in 0.2 ml of serum free medium in a 96 well cluster, flat bottomed tissue culture plate (Costar). Each fraction was added to a final concentration of 10% (v/v) in the presence, or absence of 0.25 µg/ml LPS. At 40 hours, cultures were pulsed with 1 µCi of $^3$H-TdR, harvested onto filter mats 6 hours later, and thymidine uptake assessed by scintillation spectroscopy. Numbers represent cpm$\times 10^{-3}$. FIG. 1B shows a molecular sieving [FPLC-SUPERDEX 75, Pharmacias] chromatogram (Absorbance at about 280 nm) of 20 mg of Fraction #57 (FIG. 1A), using 20 mM tris-HCL pH 8.0 buffer containing 0.45 M NaCl. Table 1B indicates the bioactivity of the peak fraction, fraction #38, assessed as described in connection with FIG. 1A. FIG. 1C shows a hydroxy apatite [HPLC-hydroxy apatite, Pharmacia] chromatogram (Absorbance at about 280 nm) of 1 mg of fraction #38 (FIG. 1B) in 1 mM NaCl using a gradient of 1–500 mM $K_2HPO_4$ buffer, pH 6.8. Table 1C indicates the bioactivity of the peak fraction, fraction #25, assessed as described in connection with FIG. 1A. The insert in the chromatogram illustrates an SDS-PAGE analysis, followed by silver staining, of roughly 5 µg of protein from fraction #25. Left track: fraction #25, right track: MW markers, from the top: 97,66,45,31,21, and 14 kD, respectively.

FIG. 2 shows the known sequence of human CD14 (SEQ ID NO:5) and aligned fragments of Bo-LAIT. Bo-LAIT fragments were generated from affinity purified colostral Bo-LAIT (see FIG. 3). Fragments corresponding to residues 235–264 and 344–355 of human CD14 were major and minor peptides, respectively, each approximately 18 kD in size, generated by CnBr cleavage, and separated by reverse phase HPLC (C8 column, Pharmacia). The fragment corresponding to residues 53–67 of human CD14 is a partial sequence of a 24 kD fragment generated by CnBr cleavage, and separated by SDS-PAGE and electroblotted onto PVDF membrane. Fragments corresponding to residues 19–36 and 151–165 of human a CD14 were generated by trypic cleavage, and separated by reverse phase HPLC (C8 column, Pharmacia). The length of the overlapping bovine sequence with the predicted sequence of human CD14 is underlined for each of the fragments. Dashes indicate the same amino acids while those differing from the human sequence are indicated.

FIG. 4A shows thymidine uptake by $5 \times 10^4$ high buoyant density mouse splenic B cells cultured as described for FIG. 1A in the presence of the indicated concentration of affinity purified Bo-LAIT that had been heat treated at 95° C. (●; lower curve) for 10 minutes, and Bo-LAIT that had not been heat treated (○; upper curve). Cultures were pulsed with $^3$H-TdR at 40 hours, harvested 6 hours later, and thymidine uptake assessed by liquid scintillation spectroscopy. The insert depicts the responses in cultures containing the indicated concentrations of LPS (0.25 µg/ml; 50 µg/ml), which had been heat treated (●), or not (○), as for nBo-LAIT. FIG. 4B shows thymidine ice in cultures that were established as described for FIG. 4A in the presence of either 0.25 µg/ml of affinity purified Bo-LAIT (two lower curves), or 50 µg/ml of LPS (two upper curves). Each of these stimuli were cultured in the presence of the indicated concentration of either polyclonal rabbit IgG anti-Bo-LAIT, #842, or normal rabbit IgG. The percent inhibition of thymidine uptake mediated by #842 IgG for both Bo-LAIT and LPS mediated stimulation is indicated in parentheses. Levels of inhibition mediated by normal rabbit IgG ranged from 9–20%, and 12–31% for Bo-LAIT and LPS stimulation, respectively. CPM directly induced by #842 IgG in isolation ranged from 454±53 to 764±69 at 0.4 and 50 µg/ml, respectively; and for normal rabbit IgG, from 297±34 to 420±31 at 0.4 and 50 µ/ml, respectively. Non-stimulated controls gave rise to 195±29 cpm for both sets of experiments.

FIGS. 6A, 6B, 6C, 6D and 6E show a comparison of nucleic acid sequence of bovine (SEQ ID NO:1), human (SEQ ID NO:2), and mouse (SEQ ID NO:3) CD14 coding regions. The first base position corresponds to the first nucleotide of the ATG codon, the last nucleotide corresponds to the third nucleotide of the TAA stop codon. Aligment was done using DNA STAR MEGALIGN software, applying the Clustal method with a weighted residue table. Human cDNA sequence (accession number P08571) and mouse. cDNA sequence (accession number P08571) used in this aligment were derived from the Swiss-Protein Database.

FIGS. 7A and 7B show a comparison of amino acid sequences of bovine (SEQ ID NO:4), human (SEQ ID NO:5), and mouse (SEQ ID NO:6) CD14 proteins. Amino acid sequences were deduced from the corresponding cDNA sequences shown in FIG. 6. DNA Star MEGALIGN software was used to generate this alignment using the method described by J. Hein (Methods in Enzymology 183:626, 1990) in conjunction with the PAM 250 residue weight table.

FIGS. 8A and 8B show primers used for amplification of Bovine CD14 cDNA coding region. FIG. 8A shows primers used for the baculovirus expression system, the "forward" sequence being identified herein as SEQ ID NO:7 and the "reverse" sequence being identified herein as SEQ ID NO:8. FIG. 8B shows primers used for the mammalian expression system, the "forward" sequence being identified herein as SEQ ID NO:9 and the "reverse" sequence being identified herein as SEQ ID NO:10.

FIG. 13A shows thymidine uptake by cord blood B cells isolated by positive selection. Cord blood leukocyte suspensions were stained with fluorescein labeled mAb specific for the pan B cell marker CD72. CD72 positive cord leukocytes were then isolated on a fluorescence activated cell sorter (FACSTAR PLUS, Becton Dickenson) resulting in purities of >98%. B cells ($1.5 \times 10^5$) were cultured as described for FIG. 1A, in the presence of no stimulus or 2 µg/ml of nBo-LAIT. B cells were also cultured in wells which had been pre-coated for 9 hours with a combination of two mAbs, one specific for human IgK [LO-HK3, (In "Rat Hybridomas and Rat Monoclonal Antibodies" ed. H. Bazin, CRC Press, Boca Raton, Fla., USA)] and one specific for human Igλ [LO-HL2, (In "Rat Hybridomas and Rat Monoclonal Antibodies" ed. H. Bazin, CRC Press, Boca Raton, Fla., USA)], each at a coating concentration of 1.5 µg/ml, without additional stimulus, or in the presence of 2 µg/ml of nBo-LAIT. Cultures were pulsed at 60 hours with 1 µCi of 3H-TdR, harvested onto filter mats 12 hours later, and thymidine uptake assessed by scintillation spectoscopy. FIG. 13B shows results obtained using tonsil B cells prepared by negative selection. Specifically, leukocyte suspensions were labelled with biotinylated mAb specific for CD3ε (Becton Dickenson), followed by avidin conjugated with iron containing "micro-beads" (Becton Dickenson). The labeled population was passed through the MACS (Becton Dickenson), and the effluent collected. This population contained <1% T cells, and >97% B cells as assessed by immunofluorescence staining with lineage specific mAbs. B cells ($1.5 \times 10^5$) were cultured as described in connection with FIG. 1A. As for cord blood B cells, tonsil B cells were cultured in the presence and absence of plate bound mAbs specific for human Igκ and λ, but in this case, wells were pre-coated using a concentration of 0.5 µg/ml of each of the mAbs. Cultures were pulsed, harvested, and thymidine uptake assessed as described for FIG. 13A.

DESCRIPTION OF PREFERRED EMBODIMENTS

Figure 1A:
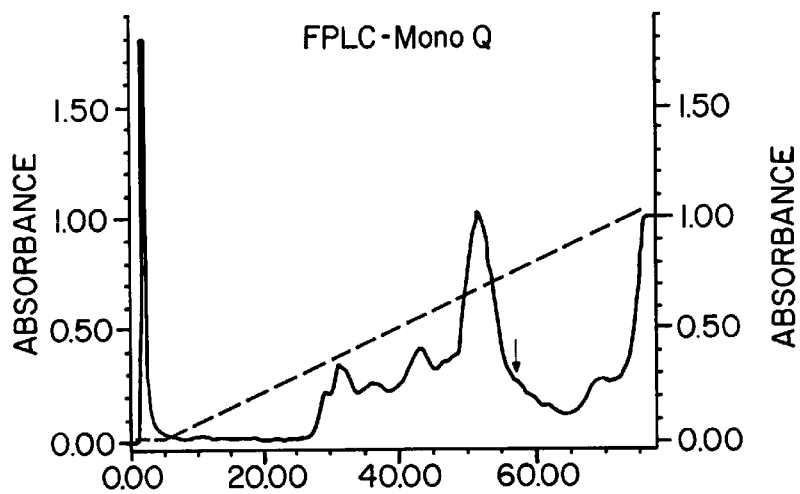
FIGS. 1A to 1C show purification of Bo-LAIT protein.

The experiments described below demonstrate purification of native bovine LAIT (lactation-associated immunotropic) protein (Bo-LAIT), also referred to herein as bovine CD14, from colostral whey. Amino acid sequence analysis of purified Bo-LAIT is shown, and homology with human CD14 is demonstrated. A method for the purification of human CD14 from colostrum, by affinity chromatography, is shown.

In vitro B cell stimulation assays are described for both affinity purified Bo-LAIT and human colostral CD14. High buoyant density resting splenic B cells derived from mouse are shown to enter and progress through cell cycle, and to differentiate into high rate immunoglobulin secreting cells in response to exposure to LAIT-protein from the two species. These activation events occur in defined serum free medium.

The isolation, cloning and sequencing of both genomic DNA and cDNA encoding bovine CD14 is described. Sequence comparisons with mouse and human CD14s, known in the literature, show the sequence relationship between Bo-LAIT and these previously known CD14s. B cell growth and differentiation activities associated with recombinant bovine CD14 are shown.

Methods for the expression of recombinant bovine CD14 in both insect and mammalian systems are described. Specifically, a baculovirus expression vector was employed in aid of expressing recombinant proteins in insect cells. Comparison of the B cell growth and differentiation properties of native Bo-LAIT (nBo-LAIT) and recombinant Bo-CD14 (rBo-LAIT) derived from the baculovirus expression system revealed that the latter was functional, and had a specific activity of roughly 1% of that of nBo-LAIT.

The mouse mammary carcinoma cell line, C127, was used as a recipient of cDNA encoding CD14 derived from the three species. These cDNAs were cloned into a bovine papilloma virus expression vector. Stable C127 transfectants were established, and recombinant CD14 proteins were isolated from supernatants of confluent C127 cultures by affinity chromatography. Western blot analyses of insect cell and C127 derived recombinant LAIT-proteins revealed that different patterns of glycosylation were generated in the two expression systems. Further, the specific activity of mammalian cell derived recombinant bovine CD14 was roughly five fold higher than that of recombinant material derived from insect cells.

A comparison of the B cell growth promoting activity supported by native Bo-LAIT and recombinant bovine CD14 derived from insect cells and mammalian cells is given. Further, growth promoting activity of native Bo-LAIT activities on human B cells, isolated from either tonsils, or from cord blood, is given.

Experiments demonstrating that bovine CD14 induces growth of B cells in which CD40 is not expressed are also given.

EXPERIMENTS

Purification of Bovine LAIT-protein

More than five liters of colostrum was obtained from the first mammary secretions of cows having just given birth.

(i) Clarified colostral whey was prepared by centrifugation of colostrum at 30,000 g for one hour. The floating lipids and the pelleted casein were discarded, and the clarified colostral whey was subjected to further fractionation.

Each fraction derived from each fractionation technique was assessed for B cell growth promoting activity in vitro. Thus, each fraction was assayed over a wide concentration range for its capacity to stimulate the growth of high buoyant density, resting B cells derived from mouse spleen, as previously described (J. Immunol. 131:581, 1983). Defined serum free medium was used throughout these analyses [IMDM (Gibco), supplemented with $5\times10^{-5}$ M 2ME, 5 µg/ml iron-saturated transferrin (Boehringer, Lewes, GB), 0.5 mg/ml delipidated BSA (Boehringer), 100 U/ml penicillin (Gibco), 100 µg/ml streptomycin (Gibco), and essential amino acids]. Fractions derived from the isolation scheme described below were tested directly, as well as in combination with a submitogenic concentration of LPS (0.25 µg/ml). As will be described, as LAIT protein approached purity, its direct mitogenic properties were revealed.

(ii) Salting out of proteins contained within colostral whey preparations was accomplished using sequential precipitation in $(NH_4)_2SO_4$. The sequence of increasing salt concentrations employed was 42%: 50%: 62%: 65% ammonium sulphate (AS). Thus, the concentration of AS in the supernatant of the material precipitated at 42% was increased to 50%; the material precipitated at 50% rescued, and the concentration of AS in the remaining supernatant increased to 62%, and so on Each AS precipitated pellet was solubilized in 10 mM Tris-HCL pH 8.0, containing 0.15 M NaCl and 1 mM AEBSF (TNAEBSF). These fractions were desalted and buffer exchanged to TNAEBSF using 10 DG columns, and assayed for bioactivity. The majority of B cell growth promoting activity was isolated in the 62% AS precipitate following the above scheme (not shown).

Figure 1B:
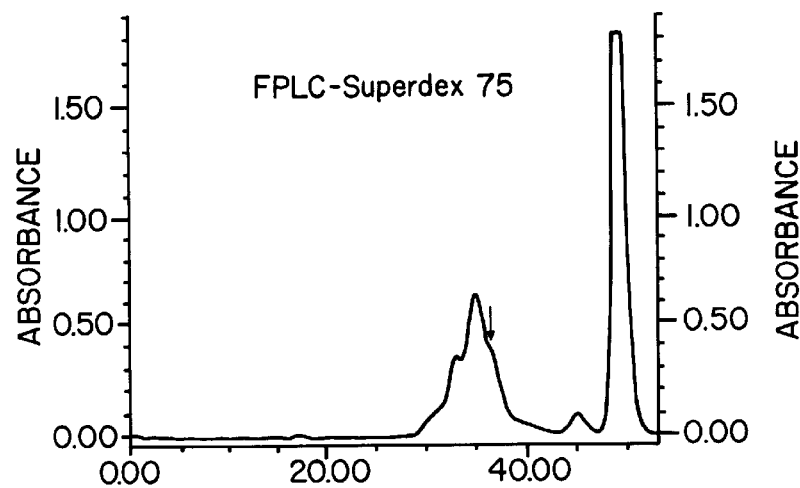

(iii) Activity was subsequently enriched, and ultimately purified using three sequential protein actionation techniques. Fifty milligrams of the 62% AS enriched fraction was applied to an anion exchange column, and the material separated using a salt gradient of 50 mM to 400 mM NaCl in 10 mM Bis-tris propane, with a simultaneous pH gradient of 7.5 to 9.5. FIG. 1A shows the elution profile from this column, and Table 1A indicates the fraction containing the peak activity, fraction #57. Twenty milligrams of fraction #57, was then applied to a molecular sieving column equilibrated in 20 mM Tris-HCL, pH 8.0 containing 0.45 M NaCl. The elution profile of this fractionation is shown in FIG. 1B and the activity of the peak fraction #38 shown in Table 1B.

TABLE 1A

|  | CPM × $10^{-3}$ |
|---|---|
| NO STIMULUS | 0.8 |
| LPS 50 µg/ml | 152.5 |
| LPS 0.25 µg/ml | 3.9 |
| FRACTION 57 + 0.25 µg/ml LPS | 108.7 |

TABLE 1B

|  | CPM × $10^{-3}$ |
|---|---|
| NO STIMULUS | 0.4 |
| LPS 50 µg/ml | 102.1 |

TABLE 1B-continued

|  | CPM × 10⁻³ |
| --- | --- |
| LPS 0.25 µg/ml | 1.3 |
| FRACTION 36 + 0.25 µg/ml LPS | 76 |

TABLE 1C

|  | CPM × 10⁻³ |
| --- | --- |
| NO STIMULUS | 0.7 |
| LPS 50 µg/ml | 135.2 |
| LPS 0.25 µg/ml | 3.5 |
| FRACTION 25 + 0.25 µg/ml LPS | 112 |

One milligram of fraction #38 was then applied to an hydroxy apatite column in 1 mM NaCl, and eluted using a gradient of 1 to 500 mM potassium phosphate buffer pH 6.8. The elution profile is shown in FIG. 1C with the associated activity shown in Table 1C.

Figure 1C:
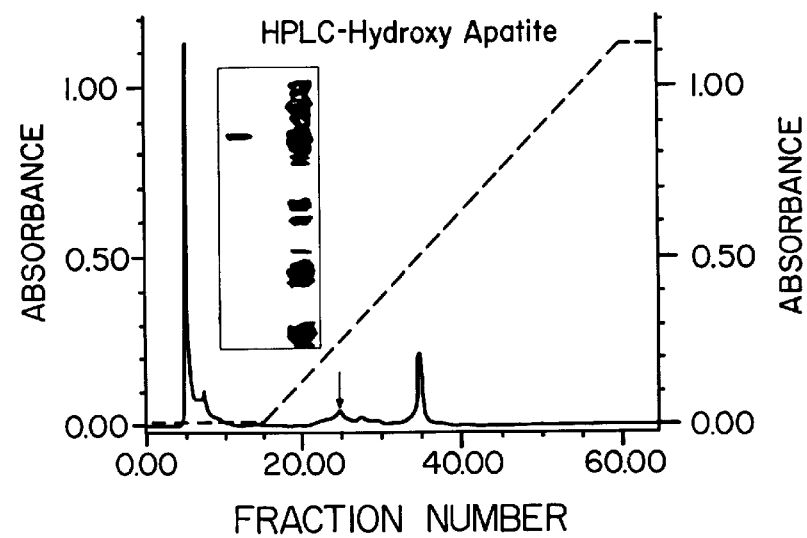

The insert in FIG. 1C represents an SDS-PAGE analysis of the fraction with peak activity followed by silver staining, and illustrates a single major band with a relative molecular mass of 46–50 kD.

Sequence Analysis of Bovine LAIT-protein

The purified Bo-LAIT was subjected to sequence analysis. The N-terminus was found to be blocked. The material was subjected to hydrolysis with either cyanogen bromide, or trypsin. Five fragments were generated and these were purified using either reverse high pressure liquid chromatography, or SDS-PAGE followed by electroblotting onto a PVDF membrane, prior to sequencing.

As illustrated in FIG. 2, the five fragments all aligned, with significant homology, to human CD14.

Affinity Purification of LAIT Protein from Bovine and Human Colostrum

Bo-LAIT isolated using classical protein fractionation techniques was used to prepare a rabbit (#842) polyclonal antibody. The IgG fraction of this antiserum was purified on Protein A-SEPHAROSE, and subsequently conjugated to SEPHAROSE 4B.

The sequence homology of Bo-LAIT and human CD14 (HuCD14) indicated that BO-LAIT might be the bovine analogue of CD14. This was further explored by generating an affinity column using available monoclonal antibody (mAb) specific for HuCD14. This antibody, 63D3 (PNAS 77:6764, 1980), was purified from the corresponding hybridoma supernatant on an affinity column comprised of mAb 187.1 [rat anti-mouse kappa (Hybridoma 1:5, 1981)], conjugated to SEPHAROSE 4B, and the purified mAb then conjugated to Sepharose 4B.

Human and bovine clarified colostral whey were sequentially salted out using ammonium sulphate, as described above. The fractions containing peak B cell growth promoting activity were then affinity purified using either the 842-Sepharose column for the bovine material, or the 63D3-Sepharose column for the human material.

Figure 3:
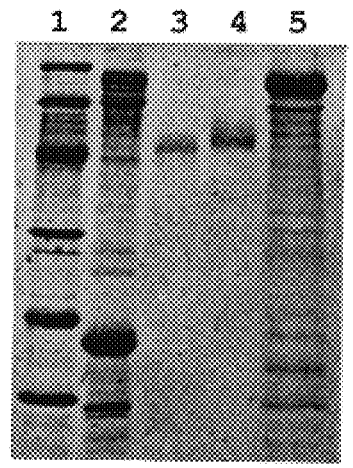
FIG. 3 shows SDS-PAGE and silver staining of affinity purified colostral LAIT-protein from bovine and human. Lane 1: MW markers, as given for FIG. 1C; lane 2: 62% $(NH_4)_2SO_4$ precipitate of bovine colostral whey; lane 3: pH 2.5 eluate from #842-SEPHAROSE affinity column; lane 4: pH 2.5 eluate from CD14 specific mAb 63D3 (PNAS 77:6764, 1980)-SEPHAROSE affinity column, loaded with material represented in lane 5; lane 5: SEPHACRYL S100 HR fractionated human colostral whey. Each of lanes 1–5 contain 5 µg of protein. Table 2 shows results obtained when $5 \times 10^4$ high buoyant density mouse splenic B cells were cultured in serum free medium in the presence of the indicated stimuli for 40 hours, pulsed with 1 µCi of $^3$H-TdR, harvested 6 hours later onto filter mats, and thymidine uptake assessed by liquid scintillation spectroscopy. Numbers represent cpm$\times 10^{-3}$. Details of the bioassay are as described for FIG. 1A. Control cpm$\times 10^{-3}$: no stimulus, 0.3; 50 µg/ml LPS, 75.0; 0.25 µg/ml LPS [LPS Ø], 0.8; and 1 µg/ml mIgM specific mAb b-7-6 (Eur. J. Immunol. 14:753, 1984), 0.7.

The SDS-PAGE analysis of affinity purified colostral Bo-LAIT, and affinity purified human colostral CD14 is shown in FIG. 3 and the associated B cell growth promoting activity is shown in Table 2. As illustrated, a predominant band was isolated from both colostral preparations, the p46–50 bovine material (FIG. 3, lane 3) and a p50–52 human molecule (FIG. 3, lane 4).

TABLE 2

|  | BOVINE #842 pH2.5 ELUATE | HUMAN 6303 pH2.5 ELUATE |
| --- | --- | --- |
| 100 ng/ml | 20.00* | 0.3 |
| 10 ng/m. | 1.49 | 0.3 |
| •+LPS ↓ | 16.5 | 21.1 |
| •+b-7-6 | 5.17 | 8.5 |

*Numbers represent cpm × 10⁻³ at 40 hours of culture.

The bioactivity shown in FIG. 3B demonstrates that affinity purified Bo-LAIT, at a concentration of 100 ng/ml, stimulated the growth of resting mouse B cells. When added at 10 ng/ml, this material was no longer mitogenic, but costimulation was achieved upon the addition of either a submitogenic concentration of LPS, or a mAb specific for mouse IgM, b-7-6 (Eur. J. Immunol. 14:753, 1984). The affinity purified human material was not by itself found to be mitogenic at concentrations tested, but at 10 ng/ml, B cell growth was stimulated with the same costimuli as efficiently as with the bovine material.

Figure 4A:
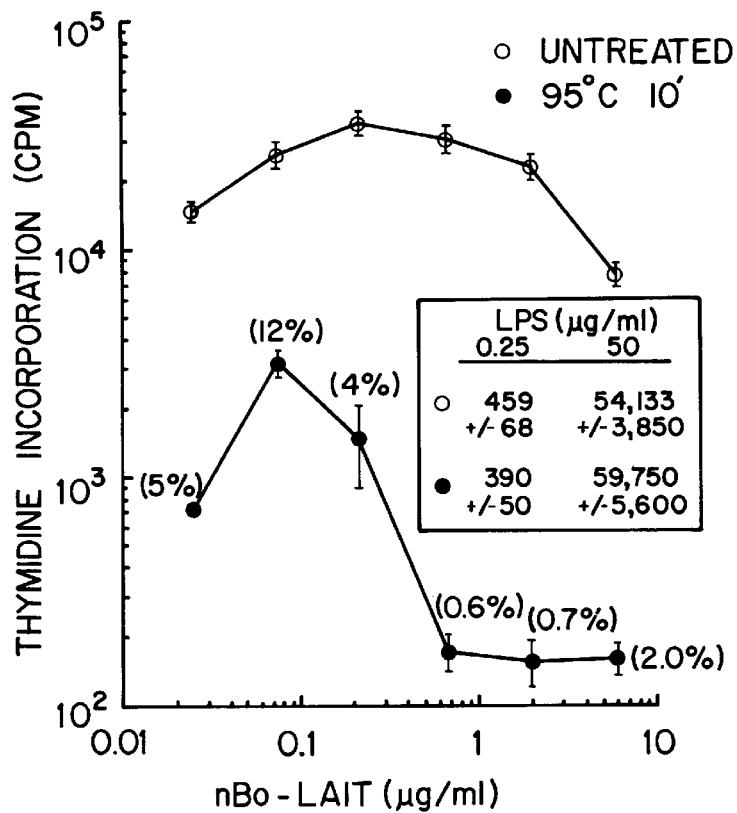
FIGS. 4A and 4B show heat lability and antibody mediated inhibition of Bo-LAIT activity.
Figure 4B:
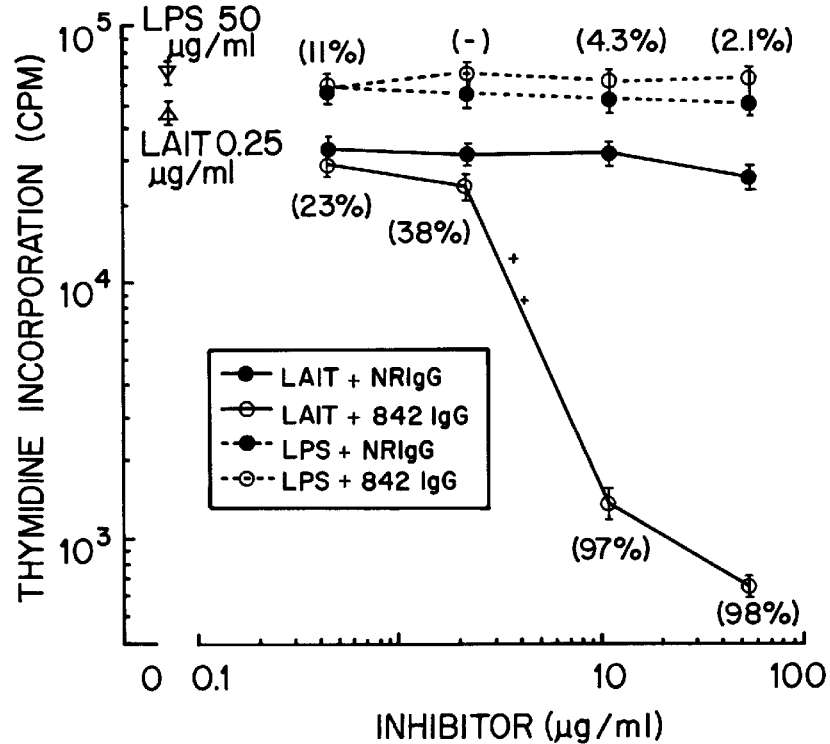

The bioactivity of Bo-LAIT is heat labile. As illustrated in FIG. 4A, treatment of affinity purified Bo-LAIT at 95° C. for 10 minutes abolishes the associated B cell growth promoting activity. Similar treatment of LPS had no effect on its activity (insert of FIG. 4A). Further, the polyclonal anti-Bo-LAIT, #842, efficiently blocked the B cell growth promoting activity of Bo-LAIT, while not affecting the activity of LPS. See the lowermost curve of FIG. 4B and insert.

Molecular Cloning of Genomic Bovine CD14

A bovine genomic EMBL3 SP6/T7 lambda library (Clontech) was screened with a 1.5 kb fragment of human CD14 cDNA (obtained from R. Ulevitch, Scripps Institute). Fifteen positive signals were obtained, and the strongest signal, clone "B2" was chosen for further analysis and cloning of bovine CD14.

Figure 5A:
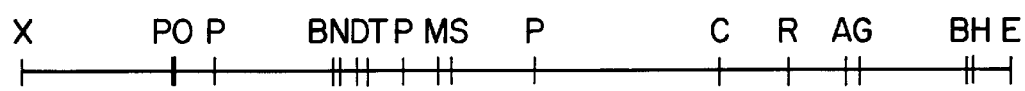
FIG. 5A shows a restriction map of the 7.1 kb EcoRI-XhoI fragment containing bovine CD14 gene. Abbreviation for restriction sites are: X, XhoI; P, PstI; O, NcoI; B, BamHI; N, NotI; D, BssHII; T, BstEII; M, SmaI; S, SacII; C, HpaI; R, EcoRV; A, SphI; G, BglII; H, HindIII; E, EcoRI.
Figure 5B:
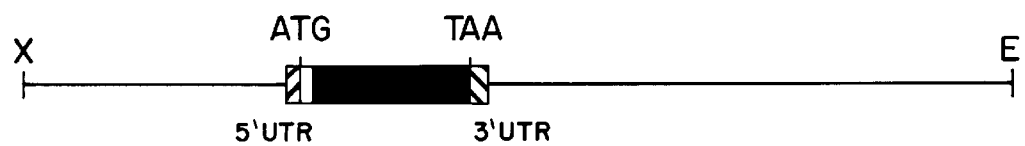
FIG. 5B is a schematic diagram of the bovine CD14 locus. The shaded area represents the coding region of the gene, the open box is an intron sequence. The dashed area in front of the ATG start codon is 5' untranslated region, and the dashed area behind the TAA stop codon is 3' untranslated region.
Figure 5C:
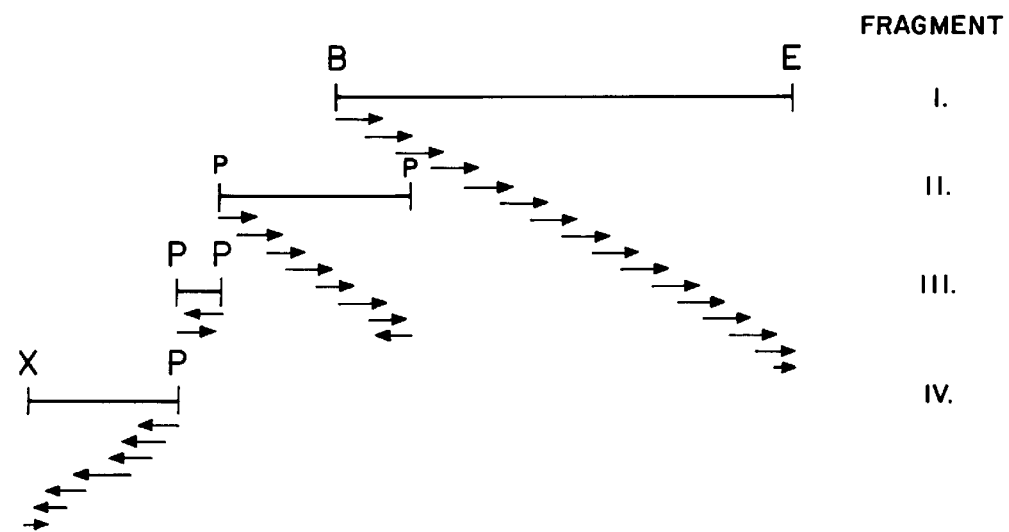
FIG. 5C is a schematic diagram showing the sequencing strategy taken. Arrows represent the direction of sequencing. The fragment number is indicated at the right (see text for detail).

Isolated and purified phage DNA from clone B2 had an insert size of roughly 15 kb. Purified DNA was digested, and a resulting 7.1 kb EcoRI-XhoI fragment, containing a homologous sequence to human CD14, was subcloned into pBLUESCRIPTSK (Stratagene). Restriction mapping, utilizing a wide range of enzymes, followed by hybridization with the human CD14 probe enabled the location of the bovine CD14 gene within the cloned fragment (FIG. 5A). Further restriction mapping was used for the subcloning of 4 shorter fragments (I–IV) into pBLUESCRIPTSK, and the subsequent sequencing of roughly 5 kb encompassing the entire bovine CD14 gene (FIG. 5C). Fragment I (EcoRI-BamIII, 3.2 kb); II (PstI-PstI, 1.35 kb); III (PstI-PstI, 0.3 kb); and IV (PstI-XhoI, 0.95 kb), were used to construct nested overlapping unidirectional deletions. These fragments provided contiguous sequence of the bovine CD14 locus. FIG. 5B depicts the organization of the bovine CD14 genomic fragment.

Molecular Cloning of Bovine CD14 cDNA

Poly(A⁺) RNA was isolated from bovine peripheral blood monocytes, and GIGAPACK II Packaging Extract (Stratagene) was used to package recombinant lambda phage DNAs. A cDNA library was prepared using the EXCELL EcoRI/CIP vector with the "TIME SAVER cDNA SYNTHESIS KIT" (Pharmacia).

The library was screened with the probe derived from the coding translated region of the bovine genomic CD14 fragment by PCR (details are provided below in the section describing the preparation of baculovirus recombinant expression vector with bovine CD14 fragment). The probe was labeled with $^{32}$P by random hexanucleotide-primed second strand synthesis (Oligolabelling Kit, Pharmacia Biotech). Screening procedures were performed under conditions of high stringency (0.1×SSC, 1%SDS, 65° C. for 3 hours). One of the clones obtained (EXCELL/BoCD14-1), contained a 1.4 kb insert, which was subcloned into pBluescript SK+, and sequenced using pBS/BoCD14 subclones containing progressive overlapping unidirectional deletions (Nested Deletion Kit, Pharmacia).

This bovine CD14 cDNA clone consists of 1327 bp. An ATG initiation codon is followed by an open reading frame of 1116 nt, and a TAA stop codon at nucleotide 1202. The open reading frame is flanked by 82 bp of 5' untranslated sequence and 122 bp of 3' untranslated sequence. A polyadenylation signal, 5'-ATTAAAA-3', is located 105 bp 3' of the termination codon.

Alignment of bovine CD14 genomic and cDNA sequences reveals that they are colinear from the start of 5' cDNA until the first and only intron (88 bp) which is found immediately after the ATG initiation codon. The remainder of the coding sequence is uninterrupted. Thus, the intron-exon organization previously described for human and mouse CD14 is precisely conserved in bovine CD14. Comparison of the translated nucleotide sequence of bovine CD14 cDNA with those of human and mouse CD14 cDNAs revealed 74.2% and 62.6% nucleotide identity in coding regions, respectively (FIG. 6).

The primary structure of the bovine CD14 protein was deduced from cDNA sequence, and consists of 374 amino acids. The first methionine is followed by a stretch of 15 hydrophobic and/or neutral residues, typical of eukaryotic signal peptides. Aligment of the amino acid sequences of bovine CD14 with human and mouse CD14 reveals 73.1% and 62.3% identity, respectively (FIG. 7). There are three potential N-linked glycosylation sites (Asn-X-Thr/Ser) all of which are conserved in human and mouse CD14. Moreover, bovine CD14 contains 10 leucine-rich repeating motifs (LXXLXL), common to both human and mouse CD14 (J. Immunol. 145:331, 1990).

Expression of Recombinant Bovine CD14 in Insect Cells

In preparing DNA fragments for producing recombinant CD14 proteins, full length fragments of CD14 translated regions were generated by PCR. Specific sets of PCR primers were designed based on sequence information obtained from bovine CD14 cDNA. The PCR primer for the 5' end contained: two recognition sequences for NheI; a Kozak sequence; an ATG initiation codon; and the first 17–21 nucleotides of translated coding region. The PCR for the 3' end contained: two recognition sequences for NheI; and last 21–24 nucleotides of translated coding region up to and excluding the TAA stop codon (FIG. 8A).

The bovine CD14 translated region was amplified using the 7.1 kb EcoRI-XhoI genomic CD14 fragment (see above) as a template PCR was carried out using Pwo DNA polymerase (Boehringer). Amplification was done by adding 5 ng of template DNA, 10 mM Tris-HCl pH 8.85, 25 mM KCl, 5 mM $(NH_4)_2SO_4$, 2 mM $MgSO_4$, 250 mM of each dNTP, 250 nM of each primer, and 5 units of Pwo DNA polymerase, in a final volume of 100 µl. The samples were amplified for 30 cycles at 70° C. annealing temperature using a DNA Thermal Cycler (Perkin Elmer).

Amplified fragments were digested with NheI, and individually subcloned downstream of the polyhedrin promoter in the baculovirus transfer vector pETL-HA (C. Richardson, OCI/Amgen). This vector Is derived from pETL (Methods in Molecular Biology 39:161, 1995), and contains a 3' 30 bp NheI-BamHI DNA fragment encoding a nonapeptide derived from influenza hemaglutinin (HA), followed by a stop codon: TAG (5'-TAC CAA TAC GAT GTT CCA GAT TAC GCT TAG-3') (SEQ ID NO:11). The recombinant transfer vectors were individually cotransfected with the wildtype baculovirus *Autographa californica* nuclear polyhedrosis virus (AcMNPV, Linear Transfection Module, Invitrogen) into Sf9 cells (Methods in Molecular Biology 39:161, 1995). The recombinant baculovirus clones were selected and purified according to established protocols (Methods in Molecular Biology 39;161, 1995). Sf9 cells were infected with recombinant baculovirus at a multiplicity of 5–10:1.

Figure 9:
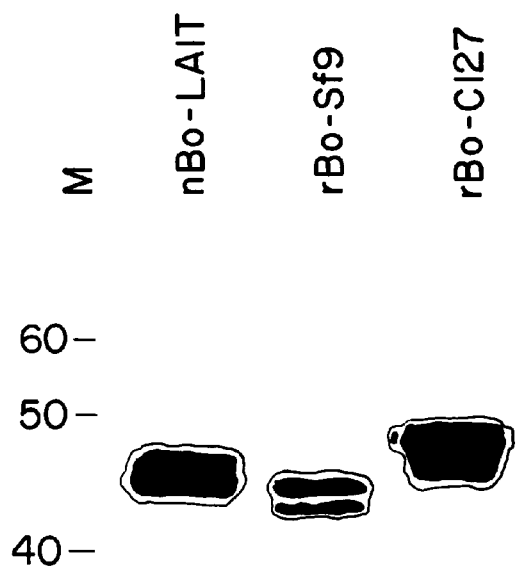
FIG. 9 shows imunoblotting of native and recombinant bovine CD14. Western blot analysis was used to evaluate and compare the sizes of native Bo-LAIT protein with recombinant CD14 proteins. 250 ng of CD14 proteins were electrophoresed on 12.5% SDS-polyacrylamide gel and electrophoretically transferred to PVDF membrane (Millipore) at 180 mA for 30 minutes. The membrane was blocked for 1 hour in 5% skim milk in TBST (20 mM Tris.HCl, pH 7.5, 150 mM NaCl, 0.025% Tween 20), followed by incubation for 1 hour with rabbit anti-Bo-LAIT #842 Ab at concentration 2.5 µg/ml in TBST supplemented with 5% skim milk. The blot was rinsed three times for 10 minutes/rinse in TBST. Goat anti-rabbit IgG conjugated with horse radish peroxidase (BioRad) was used to detect rabbit antibody. The membrane was then rinsed three times (10 minutes/rinse) with TBST. The ECL kit (Amersham) was used to visualize the proteins. Lane 1: MW markers; lane 2: nBo-LAIT-842-Sepharose affinity purified nBo-LAIT protein; lane 3: rBo-Sf9-12CA5 affinity purified, Sf9 insect cell derived recombinant bovine CD14, lane 4: rBo-C127-842-Sepharose affinity purified, C127 mouse mammary tumor cell line derived recombinant bovine CD14.

A time course analysis was performed to determine the optimum time period required for the infected Sf9 cells to secrete recombinant CD14 proteins. Immunoblot analysis of the cell media taken at different time points using the anti-HA monoclonal antibody 12CA5 (Cell 57:787, 1984), revealed that the expression of recombinant CD14 proteins reached the maximum level at 96 hours. This period was chosen in subsequent experiments for the production of recombinant proteins for bioassay (see below). Western blot analysis of Sf9 derived recombinant bovine CD14 is illustrated in FIG. 9.

Expression of Recombinant Bovine CD14 in Mammalian Cells

We used a modified version of the pBPV Episomal Mammalan Expression Vector (Pharmacia) for stable expression of recombinant bovine CD14 in mammalian cells. To enable direct selection of transformed cells, pBPV was modified by including a neomycin resistance gene, which was inserted 3.4 kb upstream of the expression cassettee. Towards this end, a 1.95 kb HindIII-XbaI fragment from pBCMGSneo (Eur. J. Immunol. 18:98, 1988) was subcloned into pCRII (Invitrogen). The recombinant construct, pCRII-neo, was purified, and the cloned fragment was amplified by PCR. PCR primers were designed such that the recognition sequence for Sal I was included at both the 5' and 3' ends. Primer sequences were complementary to the polylinker region of PCRII vector, flanking the HindIII (Primer A) and XbaI (Primer B) cloning sites.

Primer A: 5'-GCA GTC GAC ACT ATA GAA TAC TCA AGC-3' (SEQ ID NO:12)

Primer B: 5'-TTC GTC GAC ATT GGG CCC TCT AGA-3' (SEQ ID NO:13)

The final product was digested with Sal I, gel purified, and subcloned into the Sal I cloning site of pBPV in the same transcription orientation as that of the contained expression cassette. Plasmid preparations of the modified expression vector, pBPVneo-13, were generated (PLASMID MAXI KIT, Quiagen).

A DNA fragment encoding the translated region of bovine CD14 was prepared by PCR amplification of the gene in the pETL-HA vector. The 5' end PCR primer used in the amplification reaction included: an Xho I recognition sequence; followed by an Nhe I recognition sequence (present in the pETI-HA vector); a Kozak sequence; an ATG initiation codon; and the first 11 to 13 nucleotides of the translated region. The core PCR primer for the 3' end contained the HA coding sequence which was extended, as for the 5' sequences, with the inclusion of an Xho I recognition sequence. Primers are shown in FIG. 8B.

PCR was carried out using Pwo DNA polymerase (Boehringer Mannheim). Amplifications were done by adding 5 ng of DNA template, 10 mM Tris-HCl pH 8.85, 25 mM KCl, 5 mM $(NH4)_2SO4$, 2 mM $MgSO_4$, 250 mM of each dNTP, 250 nM of each primer, and 5 units of Pwo DNA polymerase in a final volume of 100 μl. The samples were amplified for 30 cycles at 70° C. annealing temperature using a DNA Thermal Cycler (Perkin Elmer).

The amplified fragments were digested with Xho I and gel purified These fragments were then subcloned into pBPVneo-13 downstream of the mouse metallothionein I promoter. Prior to the subcloning, pBPVneo-13 was pretreated with the appropriate restriction enzyme, and dephosphorylated using calf intestinal phosphatase. Recombinant plasmids were prepared using a PLASMID MAXI KIT (Quiagen).

The recombinant plasmid (pBPVneo-13-BoCD14) was transfected into the mouse mammary tumor cell line, C127 (PNAS 78:2727, 1981), using 20 μg of DNA$10^7$ cells. DNA transfer was achieved by electroporation at 960 μF/280V using a Gene pulser (BioRad Laboratories). Stable transformants were selected in the presence of 1.5 mg/ml G418 (Life Technologies).

Transfectants expressing high levels of membrane CD14 (non transfected C127 are negative for CD14) were enriched by immunofluorescence staining followed by fluorescence activated cell sorting using a Becton Dickinson FACStar Plus. The level of membrane expression of the exogenous protein correlated well with the amount of secreted CD14 rescued in 48 hour supernatants of confluent cultures of transfected C127 cells. Unlike the purification of recombinant material generated in insect cells, it was not found possible to affinity purify C127 derived material using 12CA5-Sepharose affinity columns. This might have been due to the loss of the C-terminal HA tag on recombinant proteins derived from C127 cells. As a consequence, recombinant bovine CD14 derived from C127 was affinity purified on 842-Sepharose. Immunoblot analysis of recombinant bovine CD14 derived from C127 cells is illustrated in FIG. 9.

Comparative Growth and Differentiation Promoting Activities of nBo-LAIT and LPS

Figure 10:
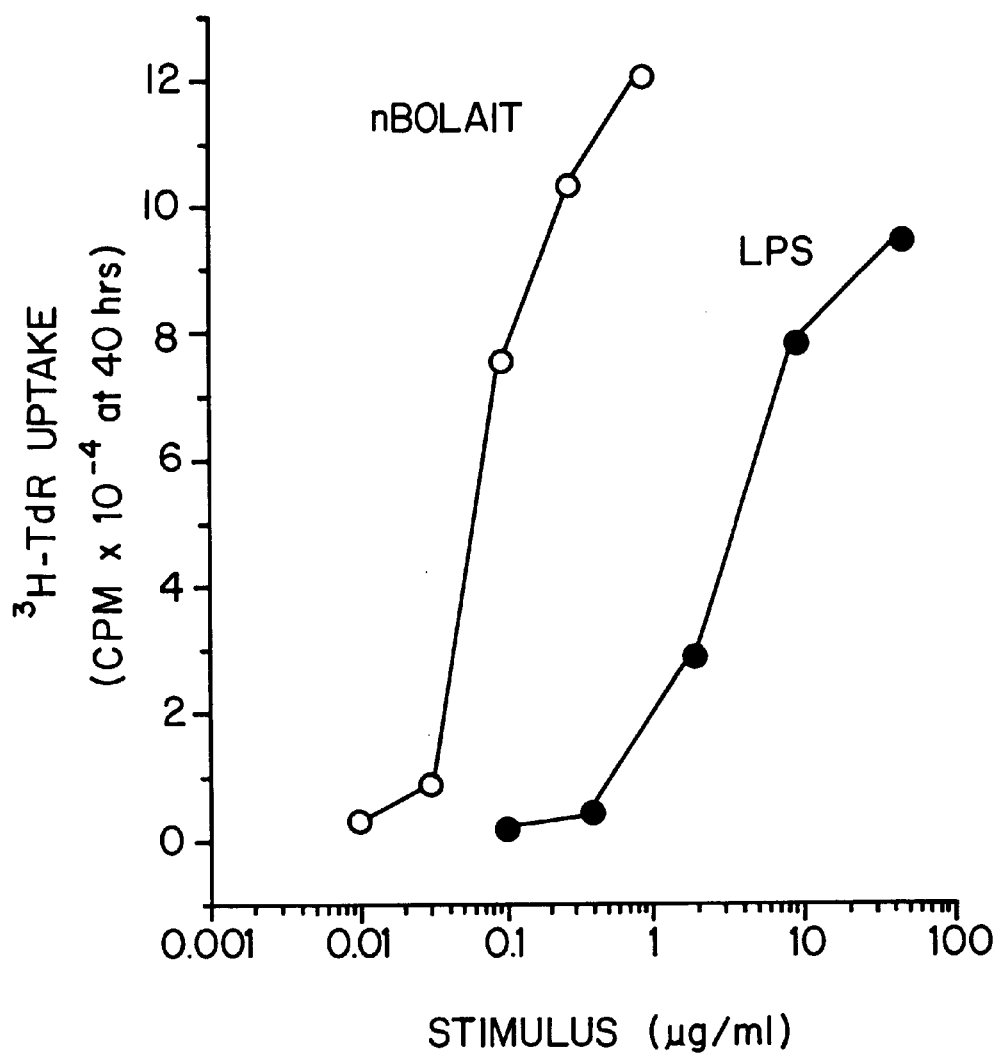
FIG. 10 shows comparative growth promoting activity of nBo-LAIT and LPS. High buoyant density resting murine splenic B cells were prepared, cultured, and harvested as described for FIG. 1A. The indicated concentrations of either affinity purified nBo-LAIT, (affinity purified as described for FIG. 1) or LPS, derived from *S. typhosa* (Difco), were added at the initiation of culture.

The results shown in FIG. 10 illustrate that native Bo-LAIT supports the growth of high buoyant density, resting, murine splenic B cells with efficiencies roughly 200-fold higher than that of LPS. Thus, nBo-LAIT at 50 ng/ml results in the induction of DNA synthesis comparable to that observed in the presence of 10 μg/ml of LPS.

Figure 11:
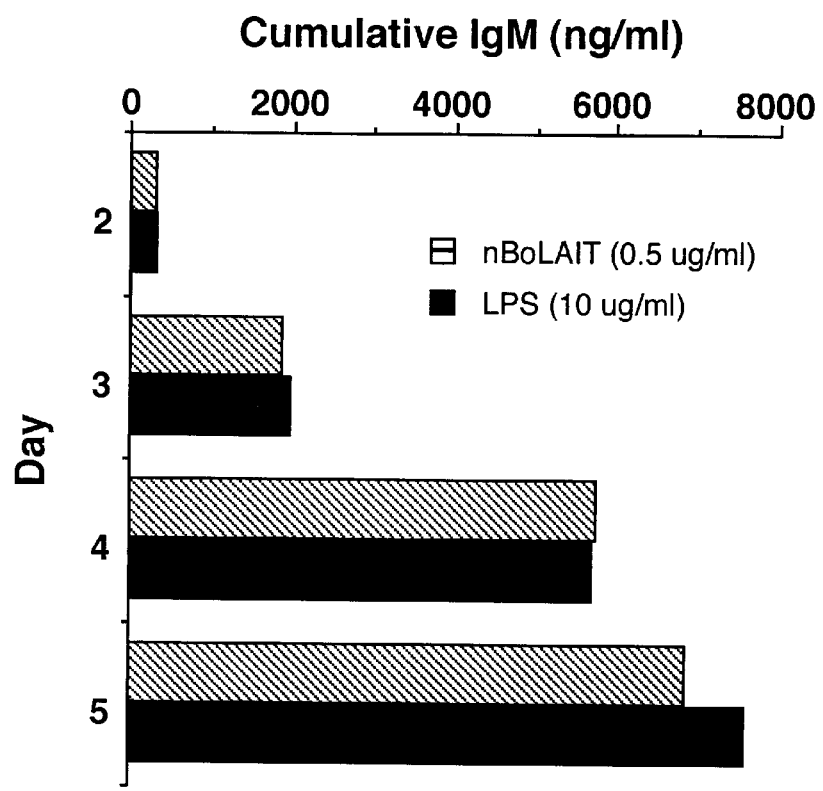
FIG. 11 shows comparative differentiation promoting activity of nBo-LAIT and LPS. High buoyant density, resting, murine splenic B cells were prepared and cultured as described for FIG. 1A. Replicate cultures were initiated using 10 µg/ml of LPS [*S. typhosa* (Difco)], or 500 ng/ml of affinity purified nBo-LAIT, and harvested at the indicated times. Cumulative IgM production was assessed by quantifying IgM present in supernatants using a commercially available ELISA kit.

The capacity of nBo-LAIT to induce B cell growth is paralleled by its capacity to induce the differentiation of high buoyant density, resting, murine B cells to immunoglobulin secretion. As illustrated in FIG. 11, the amount of cumulative IgM induced by 500 ng/ml of nBo-LAIT is comparable to that induced by 10 μg/ml of LPS. The amount of IgM secretion within a 24 hour culture period was assessed. 500 ng/ml of nBo-LAIT induced 956±10 ng/ml; 754±8.7 ng/ml; and 25±1.4 ng/ml of IgM within the 24 hour culture periods of 48–72 hours; 72–96 hours; and 96–120 hours, respectively. Corresponding values derived from cultures stimulated with 10 μg/ml of LPS were: 1442±71 ng/ml; 874±32 ng/ml; and 183±3 ng/ml, respectively. Thus, nBo-LAIT has the capacity to induce high buoyant density, resting murine B cells to immunoglobulin secretion at rates comparable to those observed when the B cells are stimulated with LPS, the most potent stimulus currently known. Further, it has the capacity to do so at concentrations of 1–10% of that of LPS.

The capacity of nBo-LAIT to induce isotype switching of murine resting B cells was also assessed. The supernatants derived from the cultures described above were also assessed for the presence of IgG isotypes. It was observed that 500 ng/ml of nBo-LAIT and 10 μg/ml of LPS induced cumulative levels (ng/ml at day 5) of IgG1: 7.0±0.1 and 5.6±0.6; IgG2a: 358±3 and 406±8; IgG2b: 8±1 and 11±2; IgG3: 75±5 and 75±0.5; and IgA: 6.5±1.5 and 5.0±0.3, respectively. Thus, nBo-LAIT, has the capacity, to induce some isotype switching by resting murine B cells in the absence of T cells.

Comparative Growth Promoting Activities of nBo- and rBo-LAIT Proteins

Figure 12:
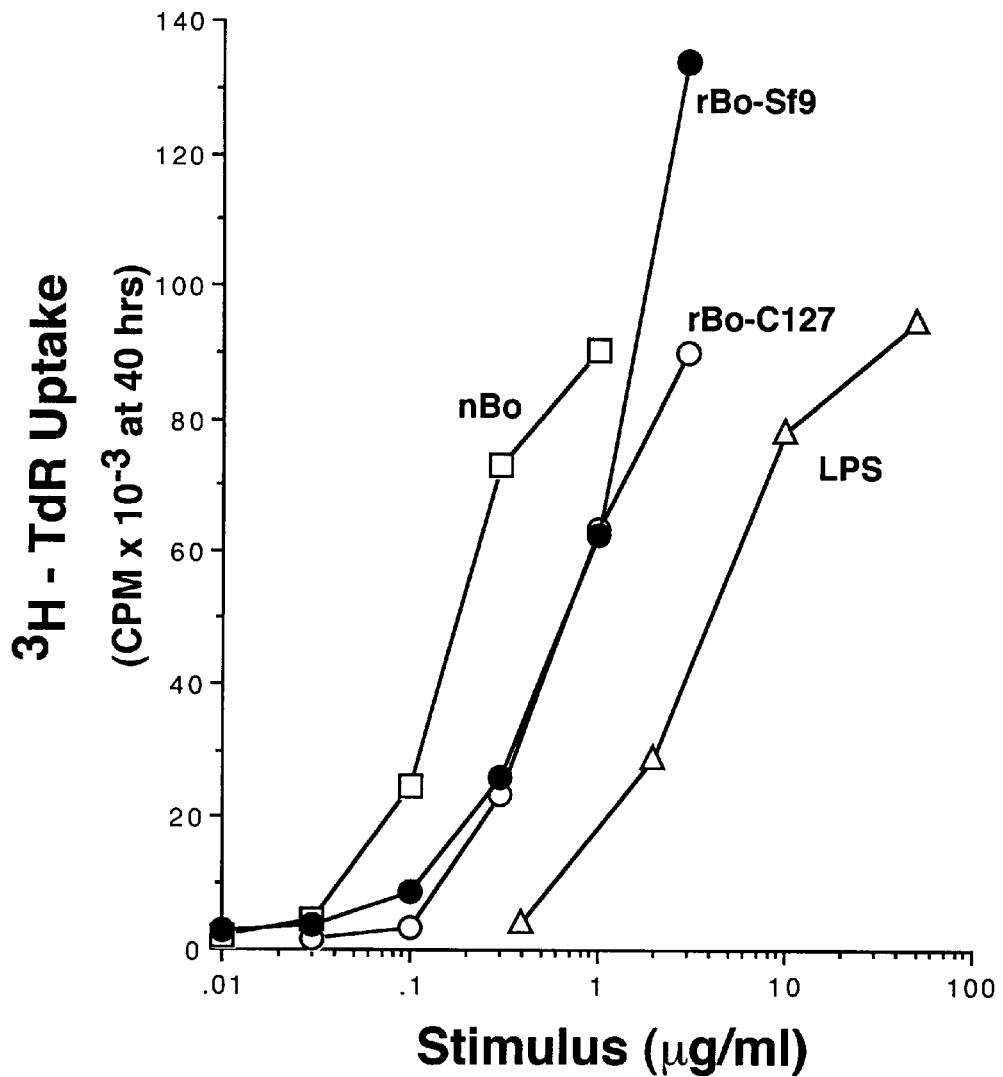
FIG. 12 shows comparative growth promoting activity of nBo- and rBo-LAIT Proteins. High buoyant density, resting, murine splenic B cells were prepared, cultured, and harvested as described for FIG. 1A. The indicated concentrations of nBo-LAIT (purified as described for FIG. 1A) and rBo-LAIT generated in either insect cells, or mammalian cells were added at the initiation of culture. Recombinant Bo-LAIT derived from insect cells was affinity purified from culture supernatants of Sf9 cells transfected with Bo-LAIT cDNA. The expression vector included a 3' 27mer encoding a nonapeptide derived from influenza hemaglutinin (HA tag). Affinity purification was achieved by passing Sf9 supernatants over Sepharose conjugated with the mAb 12CA5 (Cell 57:787, 1984), which recognizes the HA tag. Affinity purification of recombinant Bo-LAIT derived from the mammalian expression system, C127, was achieved as for nBo-LAIT, using Sepharose conjugated with IgG isolated from the polyclonal antiserum derived from rabbit 842.

Recombinant forms of bovine CD14, both to derived in insect cells and mammalian cells, have the capacity to induce the growth of high buoyant density, resting, murine B cells. As illustrated in FIG. 12, rBoCD14 derived from insect cells, and affinity purified on 12CA5-Sepharose, induces robust DNA synthesis at 1–10 μg/ml concentrations. The comparison of this recombinant form with that derived from the mammalian expression system demonstrates that the latter's specific activity is roughly 5-fold greater, supporting a potential role of distinct glycosylation as in part responsible for differences in activity (FIG. 12). However, neither recombinant form supports B cell growth at the ng/ml concentrations at which nBo-LAIT does so efficiently.

Assurance that the bioactivity mediated by nBo-LAIT isolated from bovine colostrum either by classical protein fractionation techniques, or affinity purification is mediated by the observed protein comes from the assessment of the bioactivity mediated by recombinant bovine CD14. As illustrated in FIG. 9, the apparent molecular weights of neither of the recombinant forms of bovine CD14 are identical to that of nBo-LAIT. The reason for the observed differences in apparent molecular weight is not clear but might be due to either distinct patterns of glycosylation, and/or, distinct sizes of the core proteins. Monocytes derived soluble CD14 has been documented and can be generated in one of three currently understood mechanisms, each of which would result in proteins of distinct molecule weight. It can be secreted as a full length molecule, the membrane expressed GPI linked form can be cleaved by phospholipases, and the membrane expressed GPI linked form can be cleaved by serine/threonine proteases, putatively expressed on the outer plasma membrane of the monocyte itself, and activated in as yet uncharacterized ways. Both of the recombinant forms of bovine CD14 produced here include the full length coding sequence, and thus also include the approximately 30 C-terminal residues which are required for the expression of the molecule in a GPI linked form, but are cleaved from the precursor form of the molecule prior to its association with the GPI anchor.

GROWTH and Differentiation Promoting Activity of nBo-LAIT on Human Cord Blood and Tonsil B Cells Having observed a variety of bioactivities of nBo-LAIT on murine B cells, effects on the physiology of human B cells were examined. Two sources of B cells were utilized. Since one possible role of LAIT-protein is involvement in potentiating the development of the neonatal immune system, its capacity to stimulate the growth of B cells derived from the neonate, specifically, those isolated from cord blood were assessed.

Cord blood was diluted 1:1 in phosphate buffered saline (PBS), and overlayed onto PercoII (Phamacia), ρ=1.077. The gradient was centrifuged as described in connection with FIG. 1A. The ρ=1.077/1.000 interface was harvested and washed twice in PBS supplemented with 5% fetal bovine serum (FBS). The resulting leukocyte preparation was then stained with fluorescein conjugated mAb specific for the B cell membrane marker CD72. CD72 positive cord leukocytes were then positively selected by FACS, resulting in purities of >98%. These positively selected B cells were then cultured in serum free defined medium, as for murine B cells. The only difference in the growth assays for murine and human B cells, was that the latter were pulsed with thymidine at 60 hours, for 12 hours, rather than at 40 hours, for 6 six hours.

Figure 13:
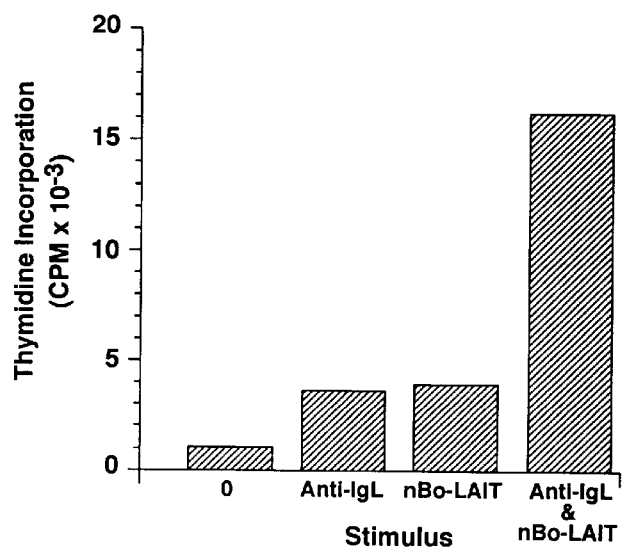
FIGS. 13A and 13B show growth promoting activity of nBo-LAIT on human B cells isolated from cord blood and tonsils.
Figure 13:
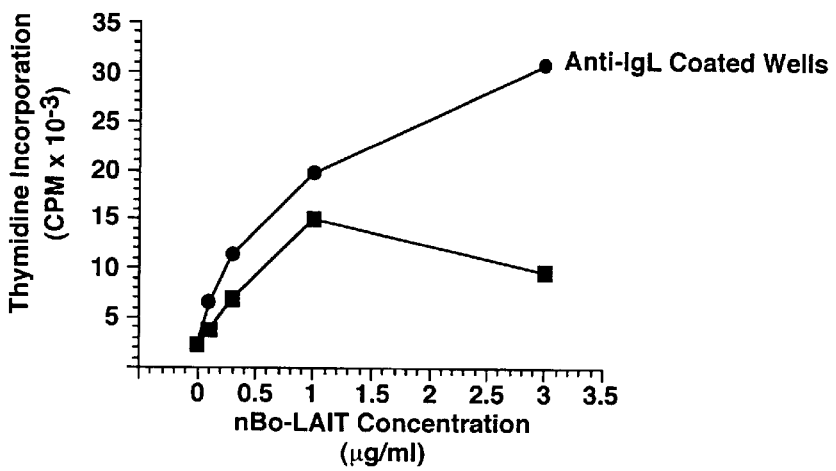

As illustrated in FIG. 13A, nBo-LAIT acts with mAbs specific for Igκ and Igλ in its capacity to induce the growth of neonatal B cells. While both immobilized (plate bound) anti-light chain mAbs and 2 μg/ml nBo-LAIT induce an increase in thymidine incorporation over background, individually, the combination of the two supported a further 5-fold increase.

These results indicate that it might be possible that LAIT protein consumed by the breast fed neonate functions as a T cell surrogate in aid of stimulating B cells which have encountered antigen to grow and possibly to differentiate into Ig secreting cells, in the absence of a fully developed T cell compartment (J. Exp. Med. 169:2149, 1989; Science 245:749, 1989; Intl. Immunol. 2:859, 1990; Intl. Immunol. 2:869, 1990).

The bioactivity of nBo-LAIT on B cells isolated from adults was assessed, in isolation, and in combination with immobilized (plate bound) anti-light chain mAbs, to stimulate B cells isolated from human tonsils.

Tonsil B cells were prepared by negative selection. Tonsil leukocytes were prepared as for cord blood leukocytes. The resulting population was labeled with biotinylated mAb specific for CD3ε (Becton Dickenson), followed by labeling with iron containing "MICRO-BEADS" (Becton Dickenson). After one wash, the labeled population was passed through a MACS (Becton Dickenson), and the effluent collected. This population contained <1% T cells, and >97% B cells as assessed by immunofluorescence staining with lineage specific mAbs. These B cells were then subjected to further fractionation on PercoII discontinuous density gradients, identical to those used for the isolation of high buoyant density murine B cells. The assays described used those B cells banding at the ρ=1.085/1.079 interface. These negatively selected, density fractionated resting B cells were cultured as described below, pulsed, and harvested as for cord blood B cells.

As illustrated in FIG. 13B, and in contrast to results obtained with B cells isolated from neonates, nBo-LAIT, in isolation, present at concentrations as low as 300 ng/ml stimulated robust growth of these resting tonsil B cells. Further, the response at some concentrations of nBo-LAIT was substantially enhanced when assessed in combination with immobilized anti-light chain mAbs (FIG. 13B).

Mature human B cells are susceptible to the growth promoting activity of nBo-LAIT, which is amplified in combination with simultaneous ligation of the B cell antigen receptor. These results characterize the potential utilization of LAIT-protein in vaccine vehicles, in aid of increasing their adjuventicity, or by possibly reducing the need for adjuvants.

LAIT-protein Induced B Cell Growth and CD40

As described above, mAbs specific for CD40, which is expressed on the membrane of B cells, have been observed to induce growth of murine B cells (Sem. in Immunol. 6:267, 1994; PNAS 83:4494, 1986; J. Immunol 140:1425, 1988;).

Figure 14:
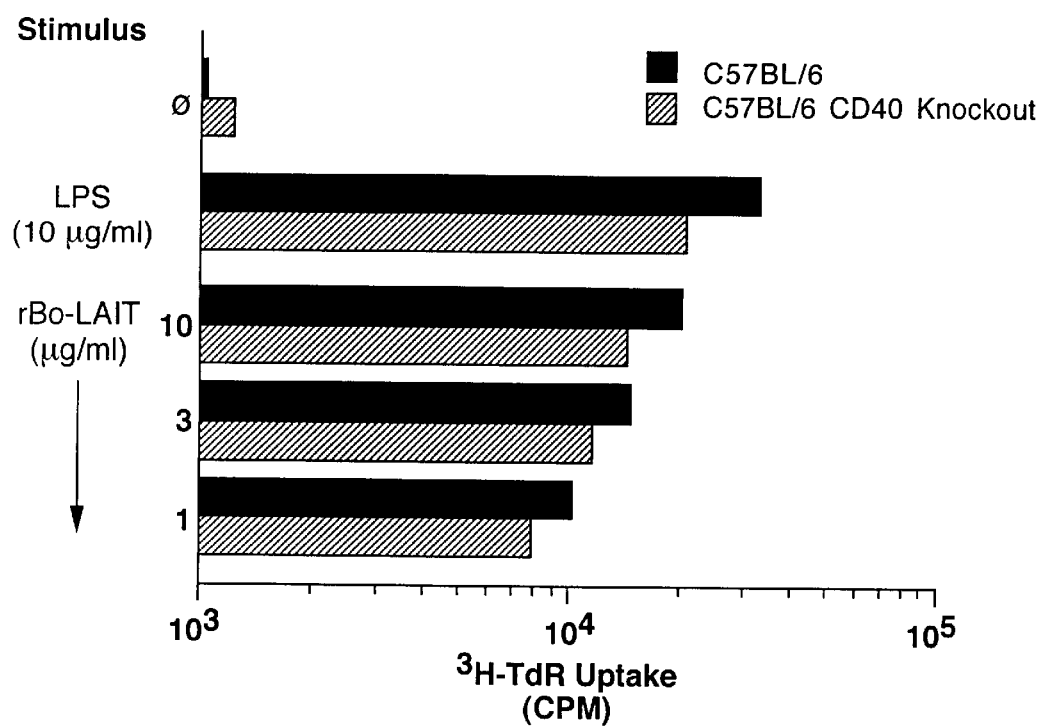
FIG. 14 shows the CD40 independence of recombinant Bo-LAIT mediated B cell adivation. High buoyant density, resting, murine B cells were isolated from either conventional C57BL/6 mice, or from CD40 deficient animals created by targeting disruption of the CD40 locus (Immunity 1:167, 1994). Cells (1.5×10) were cultured in the presence of 10 µg/ml LPS, or the indicated concentrations of rBo-LAIT derived in the insect cell expression system. Cultures were pulsed and harvested as described in connection with FIG. 1A.

To determine whether there is some relationship between anti-CD40 and LAIT-protein induced B cell activation, the capacity of RBo-LAIT to stimulate the growth of high buoyant density splenic B cells isolated from either conventional C57BL/6 mice or C57BL/6 mice in which CD40 expression was ablated through targeted gene disruption was examined (Immunity 1:167, 1994). As illustrated in FIG. 14, no differences in the responses of these B cells were observed over the concentration range of rBo-LAIT tested.

These results indicate that CD40 per se need not be involved in LAIT-protein signalling, but the possibility that second messenger generating systems utilized by CD40 and the putative membrane receptor for LAIT-protein are shared, cannot be excluded.

It may be that the transient exposure of the neonatal immune system to the B cell tropic growth and differentiation activity of colostral CD14 plays a part in development of the neonatal immune response machinery. The physiological relevance of the presence of this activity in colostrum is consistent with the observation that, as described above, T cell function in the neonate is compromised, possibly due to the presence of high concentrations of TGFβ1 and TGFβ2 in colostrum and early breast milk (J. Cell. Biol. 105:1039, 1987; Cell 49:437, 1987; EMBO J. 6:1633, 1987). As shown in Table 2, submitogenic concentrations of CD14 in combination with submitogenic concentrations of mAb specific for membrane immunoglobulin, supports the activation of B cells. CD14 might function as a T cell surrogate within the developing neonatal immune system. As such, a neonate can benefit from the use of CD14 as an infant formula additive by exposure to its immune-stimulating effects absent from synthetic formula.

A limitation of vaccination technology is the immunogenicity of a particular antigen preparation. Certain adjuvants are thought to function by recruiting and activating antigen specific T calls. CD14, as a T cell surrogate for antigen specific B cell responses, may provide an improved means to activate antigen specific B cells such that they will not only expand and differentiate into antibody secreting cells, but would, once activated, function as efficient APC for the recruitment of T cells. This would enhance both the propagation of the specific immune response and T cell mediated isotype switching.

T call immune deficiencies are known. Immunodeficiency states associated with T cell dysfunction due to the lack of expression of gp39 (which maps to the X chromosome) have been characterized: (i) X-linked hyper IgM syndrome (HIM); (ii) common viable immunodeficiency (CVI); and (iii) X-linked agammaglobulinemia (XLA). In some of these disease states (HIM), T cells isolated from patients have been shown to be unable to activate B cells (Science 259:990, 1993), and this phenotype correlates with the absence of functional gp39. In these circumstances, CD14, either targeted for the induction of specific humoral responses, or administered as a polyclonal B cell activator could function to induce/maintain levels of isogenic Ig consistent with protection against the daily barrage of potential environmental pathogen.

The presence of CD14 in colostrum is consistent with its role in stimulating B cells within the suckling neonate. The effectiveness of CD14 in aiding development of neonate immune systems can be evaluated in an animal model.

CD14 deficient females, created through targeted disruption of the CD14 locus, will be mated with either heterozygous, or CD14 deficient males. This will enable the assessment of the effects of the absence of colostral CD14 on B cell development in pups that do, or do not express CD14. Specifically, B cell ontogeny and the accumulated development of serum IgM and IgG levels will be compared, as well as the capacity of the pups to mount specific immune responses.

Further, the role that sCD14 plays in the maintenance of circulating levels of "natural" IgM can be assessed. Levels of circulating IgG and IgM are under distinct control. Serum IgG is virtually absent in mice reared in an antigen free environment, while IgM levels are unaltered. Towards addressing the potential role of sCD14 in the regulation of serum IgM levels, CD14 sufficient and deficient mice derived from the above ratings will be reared gnotobiotically.

The effectiveness of CD14 as an adjuvant in vaccination technology can be evaluated using an animal model. Bo- and Hu-CD14 will be modified with the hapten DNP. Haptenated material will be assessed for its capacity to induce polyclonal B cell activation in vitro, to insure that haptenation has not altered CD14 bioactivity. Conjugates will be injected subcutaneously, or intramuscularly, and over time, serum will be assessed for its content of specific antibody. Using another series of mice, draining lymph nodes will be collected, and contained antibody secreting cells enumerated. In addition, some recipients will be immunized with mixtures of varying amounts of CD14 and either protein or cellular antigen. Serum antibody titres, as well as antigen specific, and total Ig secreting cells will be enumerated.

Toxicity of CD14 can be evaluated in acute intravenous studies in mice, rats and monkeys. Acute subcutaneous irritation studies in rats can be performed, as well as in the long term, studies involving multiple subcutaneous and intravenous injections in the three species. Gross pathologic and histopathologic assessment will be performed, as well as serum chemistry and hematological analyses. The genotoxic potential can be assessed in mammalian cells in vitro, and in a mouse micronucleus assay. Teratogenic potential can be assessed in pregnant mice, rats, and monkeys.

In administering CD14 to a human subject, conventional pharmaceutical practice can be employed. As an additive to infant formula, it might be added to the formula at the time of manufacture. It might be prepared as a tablet or capsule, or powder for mixing just prior to administration. In the case of vaccine preparation, it might be included as part of a vaccine prepared according to otherwise standard procedures. Administration could be by any convenient means, for example, intravenous, subcutaneous, intramuscular, intraventricular, intracranial, intracapsular, intraspinal, intracisternal, intraperitoneal, or oral administration.

Parenteral formulations may be in the form of liquid solutions or suspensions.

Methods known in the art for making formulations can be found in, for example, "Remington's Pharmaceutical Sciences." Formulations for parenteral administration may, for example, contain as excipients sterile water or saline, polyalkylene glycols such as polyethylene glycol, vegetable oils, hydrogenated naphthalenes, etc, The concentration of CD14 for administration will vary depending upon, for example, the dosage to administered and the route of administration.

In terms of variation from a native amino acid sequence of CD14, at the very least, conservative substitutions could be made. Conservative substitutions are described in the patent literature, as for example, in U.S. Pat. No. 5,487,983. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, would probably be made, as could substitutions among the charged basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. Of course, it would also be expected that the greater the percentage of homology of a variant protein with a naturally occurring protein, the greater the retention of metabolic activity.

What is claimed is:

1. A method of activating B cells in a mammal in need of such activation by administering CD14 or a polypeptide portion of CD14 that activates B cells, or a conservatively substituted variant thereof that activates B cells.

2. The method of claim 1 wherein the CD14 has an amino sequence of SEQ ID NO:4, SEQ ID NO:5; or SEQ ID NO:6.

3. The method of claim 1 wherein the mammal is a human subject.

4. The method of claim 3 wherein the subject is an infant.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 1122 base pairs
        (B) TYPE: nucleic acid
        (C) STRANDEDNESS: single
        (D) TOPOLOGY: linear (xi) SEQUENCE DESCRIPTION: SEQ ID NO:1:

```
ATG GTG TGC GTG CCC TAC CTG CTG CTG CTG CTG CTG CCG TCA CTG CTG        48
Met Val Cys Val Pro Tyr Leu Leu Leu Leu Leu Leu Pro Ser Leu Leu
1               5                  10                  15

CGT GTG TCT GCG GAC ACA ACA GAA CCC TGC GAG CTG GAC GAC GAC GAT        96
```

```
Arg Val Ser Ala Asp Thr Thr Glu Pro Cys Glu Leu Asp Asp Asp
         20              25                  30

TTC CGT TGT GTC TGC AAC TTC ACG GAT CCG AAG CCT GAC TGG TCT AGC    144
Phe Arg Cys Val Cys Asn Phe Thr Asp Pro Lys Pro Asp Trp Ser Ser
         35                  40                  45

GCC GTT CAG TGT ATG GTT GCC GTC GAG GTG GAG ATC AGT GCC GGC GGC    192
Ala Val Gln Cys Met Val Ala Val Glu Val Glu Ile Ser Ala Gly Gly
         50                  55                  60

CGC AGC CTG GAA CAG TTT CTC AAG GGA GCC GAC ACC AAC CCG AAG CAG    240
Arg Ser Leu Glu Gln Phe Leu Lys Gly Ala Asp Thr Asn Pro Lys Gln
65               70                  75                  80

TAT GCT GAC ACA ATC AAG GCT CTG CGC GTT CGG CGA CTC AAG CTG GGC    288
Tyr Ala Asp Thr Ile Lys Ala Leu Arg Val Arg Arg Leu Lys Leu Gly
                 85                  90                  95

GCT GCA CAG GTT CCT GCT CAG CTT CTG GTC GCC GTT CTG CGC GCG CTC    336
Ala Ala Gln Val Pro Ala Gln Leu Leu Val Ala Val Leu Arg Ala Leu
             100                 105                 110

GGG TAC TCT CGT CTC AAG GAA CTG ACG CTT GAG GAC CTG GAG GTA ACC    384
Gly Tyr Ser Arg Leu Lys Glu Leu Thr Leu Glu Asp Leu Glu Val Thr
             115                 120                 125

GGC CCA ACG CCC CCG ACG CCT CTG GAA GCC GCT GGG CCT GCG CTC ACC    432
Gly Pro Thr Pro Pro Thr Pro Leu Glu Ala Ala Gly Pro Ala Leu Thr
         130                 135                 140

ACC CTC AGT CTG CGT AAC GTA TCG TGG ACA ACA GGA GGT GCC TGG CTC    480
Thr Leu Ser Leu Arg Asn Val Ser Trp Thr Thr Gly Gly Ala Trp Leu
145                 150                 155                 160

GGC GAA CTG CAG CAG TGG CTC AAG CCT GGG CTC AGG GTG CTG AAC ATT    528
Gly Glu Leu Gln Gln Trp Leu Lys Pro Gly Leu Arg Val Leu Asn Ile
                 165                 170                 175

GCC CAA GCA CAC TCG CTT GCC TTT CCG TGC GCA GGG CTC TCC ACC TTC    576
Ala Gln Ala His Ser Leu Ala Phe Pro Cys Ala Gly Leu Ser Thr Phe
             180                 185                 190

GAG GCG CTC ACC ACC CTA GAC CTG TCT GAC AAT CCC AGT CTC GGC GAC    624
Glu Ala Leu Thr Thr Leu Asp Leu Ser Asp Asn Pro Ser Leu Gly Asp
             195                 200                 205

ACG GGG CTG ATG GCA GCT CTC TGT CCG AAC AAG TTC CCG GCC CTC CAA    672
Thr Gly Leu Met Ala Ala Leu Cys Pro Asn Lys Phe Pro Ala Leu Gln
         210                 215                 220

TAT CTA GCG CTA CGC AAC GCG GGG ATG GAG ACG CCG AGC GGC GTG TGC    720
Tyr Leu Ala Leu Arg Asn Ala Gly Met Glu Thr Pro Ser Gly Val Cys
225                 230                 235                 240

GCG GCG CTG GCG GCA GCG AGG GTG CAG CCC CAA AGC CTG GAC CTC AGC    768
Ala Ala Leu Ala Ala Ala Arg Val Gln Pro Gln Ser Leu Asp Leu Ser
                 245                 250                 255

CAC AAC TCG CTG CGC GTC ACC GCC CCG GGT GCT ACC CGA TGT GTC TGG    816
His Asn Ser Leu Arg Val Thr Ala Pro Gly Ala Thr Arg Cys Val Trp
             260                 265                 270

CCC AGT GCA CTA AGG TCT CTC AAT TTG TCG TTC GCT GGG CTG GAG CAA    864
Pro Ser Ala Leu Arg Ser Leu Asn Leu Ser Phe Ala Gly Leu Glu Gln
             275                 280                 285

GTG CCT AAG GGA CTG CCC CCT AAG CTC AGC GTG CTT GAT CTC AGC TGC    912
Val Pro Lys Gly Leu Pro Pro Lys Leu Ser Val Leu Asp Leu Ser Cys
         290                 295                 300

AAC AAG CTA AGC AGG GAG CCG CGG CGA GAC GAG CTG CCC GAG GTA AAT    960
Asn Lys Leu Ser Arg Glu Pro Arg Arg Asp Glu Leu Pro Glu Val Asn
305                 310                 315                 320

GAC CTG ACT CTG GAC GGA AAT CCC TTT CTG GAC CCT GGA GCC CTC CAG    1008
Asp Leu Thr Leu Asp Gly Asn Pro Phe Leu Asp Pro Gly Ala Leu Gln
                 325                 330                 335

CAC CAA AAT GAC CCG ATG ATC TCC GGC GTG GTC CCA GCC TGT GCG CGT    1056
```

```
His Gln Asn Asp Pro Met Ile Ser Gly Val Val Pro Ala Cys Ala Arg
        340                 345                 350

TCT GCC TTG ACC ATG GGG GTG TCA GGA GCC CTG GCG CTG CTT CAA GGA      1104
Ser Ala Leu Thr Met Gly Val Ser Gly Ala Leu Ala Leu Leu Gln Gly
        355                 360                 365

GCC CGA GGC TTC GCG TAA                                              1122
Ala Arg Gly Phe Ala
        370
```

(2) INFORMATION FOR SEQ ID NO:2:

(i) SEQUENCE CHARACTERISTICS:
        (A) LENGTH: 1128 base pairs
        (B) TYPE: nucleic acid
        (C) STRANDEDNESS: single
        (D) TOPOLOGY: linear (xi) SEQUENCE DESCRIPTION: SEQ ID NO:2:

```
ATG GAG CGC GCG TCC TGC TTG TTG CTG CTG CTG CCG CTG GTG CAC           48
Met Glu Arg Ala Ser Cys Leu Leu Leu Leu Leu Pro Leu Val His
1               5                   10                  15

GTC TCT GCG ACC ACG CCA GAA CCT TGT GAG CTG GAC GAT GAA GAT TTC       96
Val Ser Ala Thr Thr Pro Glu Pro Cys Glu Leu Asp Asp Glu Asp Phe
            20                  25                  30

CGC TGC GTC TGC AAC TTC TCC GAA CCT CAG CCC GAC TGG TCC GAA GCC      144
Arg Cys Val Cys Asn Phe Ser Glu Pro Gln Pro Asp Trp Ser Glu Ala
        35                  40                  45

TTC CAG TGT GTG TCT GCA GTA GAG GTG GAG ATC CAT GCC GGC GGT CTC      192
Phe Gln Cys Val Ser Ala Val Glu Val Glu Ile His Ala Gly Gly Leu
    50                  55                  60

AAC CTA GAG CCG TTT CTA AAG CGC GTC GAT GCG GAC GCC GAC CCG CGG      240
Asn Leu Glu Pro Phe Leu Lys Arg Val Asp Ala Asp Ala Asp Pro Arg
65                  70                  75                  80

CAG TAT GCT GAC ACG GTC AAG GCT CTC CGC GTG CGG CGG CTC ACA GTG      288
Gln Tyr Ala Asp Thr Val Lys Ala Leu Arg Val Arg Arg Leu Thr Val
                85                  90                  95

GGA GCC GCA CAG GTT CCT GCT CAG CTA CTG GTA GGC GCC CTG CGT GTG      336
Gly Ala Ala Gln Val Pro Ala Gln Leu Leu Val Gly Ala Leu Arg Val
            100                 105                 110

CTA GCG TAC TCC CGC CTC AAG GAA CTG ACG CTC GAG GAC CTA AAG ATA      384
Leu Ala Tyr Ser Arg Leu Lys Glu Leu Thr Leu Glu Asp Leu Lys Ile
        115                 120                 125

ACC GGC ACC ATG CCT CCG CTG CCT CTG GAA GCC ACA GGA CTT GCA CTT      432
Thr Gly Thr Met Pro Pro Leu Pro Leu Glu Ala Thr Gly Leu Ala Leu
    130                 135                 140

TCC AGC TTG CGC CTA CGC AAC GTG TCG TGG GCG ACA GGG CGT TCT TGG      480
Ser Ser Leu Arg Leu Arg Asn Val Ser Trp Ala Thr Gly Arg Ser Trp
145                 150                 155                 160

CTC GCC GAG CTG CAG CAG TGG CTC AAG CCA GGC CTC AAG GTA CTG AGC      528
Leu Ala Glu Leu Gln Gln Trp Leu Lys Pro Gly Leu Lys Val Leu Ser
                165                 170                 175

ATT GCC CAA GCA CAC TCG CCT GCC TTT TCC TGC GAA CAG GTT CGC GCC      576
Ile Ala Gln Ala His Ser Pro Ala Phe Ser Cys Glu Gln Val Arg Ala
            180                 185                 190

TTC CCG GCC CTT ACC AGC CTA GAC CTG TCT GAC AAT CCT GGA CTG GGC      624
Phe Pro Ala Leu Thr Ser Leu Asp Leu Ser Asp Asn Pro Gly Leu Gly
        195                 200                 205

GAA CGC GGA CTG ATG GCG GCT CTC TGT CCC CAC AAG TTC CCG GCC ATC      672
Glu Arg Gly Leu Met Ala Ala Leu Cys Pro His Lys Phe Pro Ala Ile
    210                 215                 220

CAG AAT CTA GCG CTG CGC AAC ACA GGA ATG GAG ACG CCC ACA GGC GTG      720
Gln Asn Leu Ala Leu Arg Asn Thr Gly Met Glu Thr Pro Thr Gly Val
```

```
                      225                 230                 235                 240
TGC GCC GCA CTG GCG GCG GCA GGT GTG CAG CCC CAC AGC CTA GAC CTC               768
Cys Ala Ala Leu Ala Ala Ala Gly Val Gln Pro His Ser Leu Asp Leu
                245                 250                 255

AGC CAC AAC TCG CTG CGC GCC ACC GTA AAC CCT AGC GCT CCG AGA TGC               816
Ser His Asn Ser Leu Arg Ala Thr Val Asn Pro Ser Ala Pro Arg Cys
                260                 265                 270

ATG TGG TCC AGC GCC CTG AAC TCC CTC AAT CTG TCG TTC GCT GGG CTG               864
Met Trp Ser Ser Ala Leu Asn Ser Leu Asn Leu Ser Phe Ala Gly Leu
                275                 280                 285

GAA CAG GTG CCT AAA GGA CTG CCA GCC AAG CTC AGA GTG CTC GAT CTC               912
Glu Gln Val Pro Lys Gly Leu Pro Ala Lys Leu Arg Val Leu Asp Leu
                290                 295                 300

AGC TGC AAC AGA CTG AAC AGG GCG CCG CAG CCT GAC GAG CTG CCC GAG               960
Ser Cys Asn Arg Leu Asn Arg Ala Pro Gln Pro Asp Glu Leu Pro Glu
305                 310                 315                 320

GTG GAT AAC CTG ACA CTG GAC GGG AAT CCC TTC CTG GTC CCT GGA ACT              1008
Val Asp Asn Leu Thr Leu Asp Gly Asn Pro Phe Leu Val Pro Gly Thr
                325                 330                 335

GCC CTC CCC CAC GAG GGC TCA ATG AAC TCC GGC GTG GTC CCA GCC TGT              1056
Ala Leu Pro His Glu Gly Ser Met Asn Ser Gly Val Val Pro Ala Cys
                340                 345                 350

GCA CGT TCG ACC CTG TCG GTG GGG GTG TCG GGA ACC CTG GTG CTG CTC              1104
Ala Arg Ser Thr Leu Ser Val Gly Val Ser Gly Thr Leu Val Leu Leu
                355                 360                 365

CAA GGG GCC CGG GGC TTT GCC TAA                                              1128
Gln Gly Ala Arg Gly Phe Ala
                370                 375

(2) INFORMATION FOR SEQ ID NO:3:

(i) SEQUENCE CHARACTERISTICS:
        (A) LENGTH: 1101 base pairs
        (B) TYPE: nucleic acid
        (C) STRANDEDNESS: single
        (D) TOPOLOGY: linear (xi) SEQUENCE DESCRIPTION: SEQ ID NO:3:

ATG GAG CGT GTG CTT GGC TTG TTG CTG TTG CTT CTG GTG CAC GCC TCT                48
Met Glu Arg Val Leu Gly Leu Leu Leu Leu Leu Val His Ala Ser
1                   5                  10                  15

CCC GCC CCA CCA GAG CCC TGC GAG CTA GAC GAG GAA AGT TGT TCC TGC                96
Pro Ala Pro Pro Glu Pro Cys Glu Leu Asp Glu Glu Ser Cys Ser Cys
                20                  25                  30

AAC TTC TCA GAT CCG AAG CCA GAT TGG TCC AGC GCT TTC AAT TGT TTG               144
Asn Phe Ser Asp Pro Lys Pro Asp Trp Ser Ser Ala Phe Asn Cys Leu
                35                  40                  45

GGG GCG GCA GAT GTG GAA TTG TAC GGC GGC GGC CGC AGC CTG GAA TAC               192
Gly Ala Ala Asp Val Glu Leu Tyr Gly Gly Gly Arg Ser Leu Glu Tyr
                50                  55                  60

CTT CTA AAG CGT GTG GAC ACG GAA GCA GAT CTG GGG CAG TTC ACT GAT               240
Leu Leu Lys Arg Val Asp Thr Glu Ala Asp Leu Gly Gln Phe Thr Asp
65                  70                  75                  80

ATT ATC AAG TCT CTG TCC TTA AAG CGG CTT ACG GTG CGG GCC GCG CGG               288
Ile Ile Lys Ser Leu Ser Leu Lys Arg Leu Thr Val Arg Ala Ala Arg
                85                  90                  95

ATT CCT AGT CGG ATT CTA TTC GGA GCC CTG CGT GTG CTC GGG ATT TCC               336
Ile Pro Ser Arg Ile Leu Phe Gly Ala Leu Arg Val Leu Gly Ile Ser
                100                 105                 110

GGC CTC CAG GAA CTG ACT CTT GAA AAT CTC GAG GTA ACC GGC ACC GCG               384
Gly Leu Gln Glu Leu Thr Leu Glu Asn Leu Glu Val Thr Gly Thr Ala
                115                 120                 125
```

```
CCG CCA CCG CTT CTG GAA GCC ACC GGA CCC GAT CTC AAC ATC TTG AAC    432
Pro Pro Pro Leu Leu Glu Ala Thr Gly Pro Asp Leu Asn Ile Leu Asn
        130                 135                 140

CTC CGC AAC GTG TCG TGG GCA ACA AGG GAT GCC TGG CTC GCA GAA CTG    480
Leu Arg Asn Val Ser Trp Ala Thr Arg Asp Ala Trp Leu Ala Glu Leu
145                 150                 155                 160

CAG CAG TGG CTA AAG CCT GGA CTC AAG GTA CTG AGT ATT GCC CAA GCA    528
Gln Gln Trp Leu Lys Pro Gly Leu Lys Val Leu Ser Ile Ala Gln Ala
                165                 170                 175

CAC TCA CTC AAC TTT TCC TGC GAA CAG GTC CGC GTC TTC CCT GCC CTC    576
His Ser Leu Asn Phe Ser Cys Glu Gln Val Arg Val Phe Pro Ala Leu
        180                 185                 190

TCC ACC TTA GAC CTG TCT GAC AAT CCT GAA TTG GGC GAG AGA GGA CTG    624
Ser Thr Leu Asp Leu Ser Asp Asn Pro Glu Leu Gly Glu Arg Gly Leu
        195                 200                 205

ATC TCA GCC CTC TGT CCC CTC AAG TTC CCG ACC CTC CAA GTT TTA GCG    672
Ile Ser Ala Leu Cys Pro Leu Lys Phe Pro Thr Leu Gln Val Leu Ala
        210                 215                 220

CTG CGT AAC GCG GGG ATG GAG ACG CCC AGC GGC GTG TGC TCT GCG CTG    720
Leu Arg Asn Ala Gly Met Glu Thr Pro Ser Gly Val Cys Ser Ala Leu
225                 230                 235                 240

GCC GCA GCA AGG GTA CAG CTG CAA GGA CTA GAC CTT AGT CAC AAT TCA    768
Ala Ala Ala Arg Val Gln Leu Gln Gly Leu Asp Leu Ser His Asn Ser
                245                 250                 255

CTG CGG GAT GCT GCA GGC GCT CCG AGT TGT GAC TGG CCC AGT CAG CTA    816
Leu Arg Asp Ala Ala Gly Ala Pro Ser Cys Asp Trp Pro Ser Gln Leu
        260                 265                 270

AAC TCG CTC AAT CTG TCT TTC ACT GGG CTG AAG CAG GTA CCT AAA GGG    864
Asn Ser Leu Asn Leu Ser Phe Thr Gly Leu Lys Gln Val Pro Lys Gly
        275                 280                 285

CTG CCA GCC AAG CTC AGC GTG CTG GAT CTC AGT TAC AAC AGG CTG GAT    912
Leu Pro Ala Lys Leu Ser Val Leu Asp Leu Ser Tyr Asn Arg Leu Asp
290                 295                 300

AGG AAC CCT AGC CCA GAT GAG CTG CCC CAA GTG GGG AAC CTG TCA CTT    960
Arg Asn Pro Ser Pro Asp Glu Leu Pro Gln Val Gly Asn Leu Ser Leu
305                 310                 315                 320

AAA GGA AAT CCC TTT TTG GAC TCT GAA TCC CAC TCG GAG AAG TTT AAC   1008
Lys Gly Asn Pro Phe Leu Asp Ser Glu Ser His Ser Glu Lys Phe Asn
                325                 330                 335

TCT GGC GTA GTC ACC GCC GGA GCT CCA TCA TCC CAA GCA GTG GCC TTG   1056
Ser Gly Val Val Thr Ala Gly Ala Pro Ser Ser Gln Ala Val Ala Leu
        340                 345                 350

TCA GGA ACT CTG GCT TTG CTC CTA GGA GAT CGC CTC TTT GTT TAA      1101
Ser Gly Thr Leu Ala Leu Leu Leu Gly Asp Arg Leu Phe Val
        355                 360                 365
```

(2) INFORMATION FOR SEQ ID NO:4:

(i) SEQUENCE CHARACTERISTICS:
        (A) LENGTH: 373 amino acids
        (B) TYPE: amino acid
        (C) STRANDEDNESS: single
        (D) TOPOLOGY: linear (xi) SEQUENCE DESCRIPTION: SEQ ID NO:4:

```
Met Val Cys Val Pro Tyr Leu Leu Leu Leu Leu Pro Ser Leu Leu
1               5                   10                  15

Arg Val Ser Ala Asp Thr Thr Glu Pro Cys Glu Leu Asp Asp Asp
                20                  25                  30

Phe Arg Cys Val Cys Asn Phe Thr Asp Pro Lys Pro Asp Trp Ser Ser
        35                  40                  45
```

```
Ala Val Gln Cys Met Val Ala Val Glu Val Glu Ile Ser Ala Gly Gly
    50                  55                  60
Arg Ser Leu Glu Gln Phe Leu Lys Gly Ala Asp Thr Asn Pro Lys Gln
65                  70                  75                  80
Tyr Ala Asp Thr Ile Lys Ala Leu Arg Val Arg Leu Lys Leu Gly
                    85                  90                  95
Ala Ala Gln Val Pro Ala Gln Leu Leu Ala Val Leu Arg Ala Leu
                100                 105                 110
Gly Tyr Ser Arg Leu Lys Glu Leu Thr Leu Glu Asp Leu Glu Val Thr
                115                 120                 125
Gly Pro Thr Pro Pro Thr Pro Leu Glu Ala Ala Gly Pro Ala Leu Thr
    130                 135                 140
Thr Leu Ser Leu Arg Asn Val Ser Trp Thr Thr Gly Gly Ala Trp Leu
145                 150                 155                 160
Gly Glu Leu Gln Gln Trp Leu Lys Pro Gly Leu Arg Val Leu Asn Ile
                    165                 170                 175
Ala Gln Ala His Ser Leu Ala Phe Pro Cys Ala Gly Leu Ser Thr Phe
                180                 185                 190
Glu Ala Leu Thr Thr Leu Asp Leu Ser Asp Asn Pro Ser Leu Gly Asp
            195                 200                 205
Thr Gly Leu Met Ala Ala Leu Cys Pro Asn Lys Phe Pro Ala Leu Gln
            210                 215                 220
Tyr Leu Ala Leu Arg Asn Ala Gly Met Glu Thr Pro Ser Gly Val Cys
225                 230                 235                 240
Ala Ala Leu Ala Ala Ala Arg Val Gln Pro Gln Ser Leu Asp Leu Ser
                245                 250                 255
His Asn Ser Leu Arg Val Thr Ala Pro Gly Ala Thr Arg Cys Val Trp
                260                 265                 270
Pro Ser Ala Leu Arg Ser Leu Asn Leu Ser Phe Ala Gly Leu Glu Gln
            275                 280                 285
Val Pro Lys Gly Leu Pro Pro Lys Leu Ser Val Leu Asp Leu Ser Cys
            290                 295                 300
Asn Lys Leu Ser Arg Glu Pro Arg Arg Asp Glu Leu Pro Glu Val Asn
305                 310                 315                 320
Asp Leu Thr Leu Asp Gly Asn Pro Phe Leu Asp Pro Gly Ala Leu Gln
                325                 330                 335
His Gln Asn Asp Pro Met Ile Ser Gly Val Val Pro Ala Cys Ala Arg
                340                 345                 350
Ser Ala Leu Thr Met Gly Val Ser Gly Ala Leu Ala Leu Leu Gln Gly
                355                 360                 365
Ala Arg Gly Phe Ala
        370

(2) INFORMATION FOR SEQ ID NO:5:

(i) SEQUENCE CHARACTERISTICS:
        (A) LENGTH: 375 amino acids
        (B) TYPE: amino acid
        (C) STRANDEDNESS: single
        (D) TOPOLOGY: linear (xi) SEQUENCE DESCRIPTION: SEQ ID NO:5:

Met Glu Arg Ala Ser Cys Leu Leu Leu Leu Leu Leu Pro Leu Val His
1               5                   10                  15
Val Ser Ala Thr Thr Pro Glu Pro Cys Glu Leu Asp Asp Glu Asp Phe
                20                  25                  30
```

```
Arg Cys Val Cys Asn Phe Ser Glu Pro Gln Pro Asp Trp Ser Glu Ala
            35                  40                  45

Phe Gln Cys Val Ser Ala Val Glu Val Glu Ile His Ala Gly Gly Leu
        50                  55                  60

Asn Leu Glu Pro Phe Leu Lys Arg Val Asp Ala Asp Ala Asp Pro Arg
 65                  70                  75                  80

Gln Tyr Ala Asp Thr Val Lys Ala Leu Arg Val Arg Arg Leu Thr Val
                 85                  90                  95

Gly Ala Ala Gln Val Pro Ala Gln Leu Val Gly Ala Leu Arg Val
                100                 105                 110

Leu Ala Tyr Ser Arg Leu Lys Glu Leu Thr Leu Glu Asp Leu Lys Ile
            115                 120                 125

Thr Gly Thr Met Pro Pro Leu Pro Leu Glu Ala Thr Gly Leu Ala Leu
        130                 135                 140

Ser Ser Leu Arg Leu Arg Asn Val Ser Trp Ala Thr Gly Arg Ser Trp
145                 150                 155                 160

Leu Ala Glu Leu Gln Gln Trp Leu Lys Pro Gly Leu Lys Val Leu Ser
                165                 170                 175

Ile Ala Gln Ala His Ser Pro Ala Phe Ser Tyr Glu Gln Val Arg Ala
            180                 185                 190

Phe Pro Ala Leu Thr Ser Leu Asp Leu Ser Asp Asn Pro Gly Leu Gly
        195                 200                 205

Glu Arg Gly Leu Met Ala Ala Leu Cys Pro His Lys Phe Pro Ala Ile
    210                 215                 220

Gln Asn Leu Ala Leu Arg Asn Thr Gly Met Glu Thr Pro Thr Gly Val
225                 230                 235                 240

Cys Ala Ala Leu Ala Ala Ala Gly Val Gln Pro His Ser Leu Asp Leu
                245                 250                 255

Ser His Asn Ser Leu Arg Ala Thr Val Asn Pro Ser Ala Pro Arg Cys
            260                 265                 270

Met Trp Ser Ser Ala Leu Asn Ser Leu Asn Leu Ser Phe Ala Gly Leu
        275                 280                 285

Glu Gln Val Pro Lys Gly Leu Pro Ala Lys Leu Arg Val Leu Asp Leu
    290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys
            340                 345                 350

Ala Arg Ser Thr Leu Ser Val Gly Val Ser Gly Thr Leu Val Leu Leu
        355                 360                 365

Gln Gly Ala Arg Gly Phe Ala
    370                 375

(2) INFORMATION FOR SEQ ID NO:6:

(i) SEQUENCE CHARACTERISTICS:
        (A) LENGTH: 366 amino acids
        (B) TYPE: amino acid
        (C) STRANDEDNESS: single
        (D) TOPOLOGY: linear (xi) SEQUENCE DESCRIPTION: SEQ ID NO:6:

Met Glu Arg Val Leu Gly Leu Leu Leu Leu Leu Val His Ala Ser
 1               5                  10                  15
```

-continued

```
Pro Ala Pro Pro Glu Pro Cys Glu Leu Asp Glu Ser Cys Ser Cys
            20                  25                  30

Asn Phe Ser Asp Pro Lys Pro Asp Trp Ser Ser Ala Phe Asn Cys Leu
        35                  40                  45

Gly Ala Ala Asp Val Glu Leu Tyr Gly Gly Arg Ser Leu Glu Tyr
50                  55                  60

Leu Leu Lys Arg Val Asp Thr Glu Ala Asp Leu Gly Gln Phe Thr Asp
65                  70                  75                  80

Ile Ile Lys Ser Leu Ser Leu Lys Arg Leu Thr Val Arg Ala Ala Arg
                85                  90                  95

Ile Pro Ser Arg Ile Leu Phe Gly Ala Leu Arg Val Leu Gly Ile Ser
                100                 105                 110

Gly Leu Gln Glu Leu Thr Leu Glu Asn Leu Glu Val Thr Gly Thr Ala
            115                 120                 125

Pro Pro Pro Leu Leu Glu Ala Thr Gly Pro Asp Leu Asn Ile Leu Asn
        130                 135                 140

Leu Arg Asn Val Ser Trp Ala Thr Arg Asp Ala Trp Leu Ala Glu Leu
145                 150                 155                 160

Gln Gln Trp Leu Lys Pro Gly Leu Lys Val Leu Ser Ile Ala Gln Ala
                165                 170                 175

His Ser Leu Asn Phe Ser Cys Glu Gln Val Arg Val Phe Pro Ala Leu
                180                 185                 190

Ser Thr Leu Asp Leu Ser Asp Asn Pro Glu Leu Gly Glu Arg Gly Leu
        195                 200                 205

Ile Ser Ala Leu Cys Pro Leu Lys Phe Pro Thr Leu Gln Val Leu Ala
    210                 215                 220

Leu Arg Asn Ala Gly Met Glu Thr Pro Ser Gly Val Cys Ser Ala Leu
225                 230                 235                 240

Ala Ala Ala Arg Val Gln Leu Gln Gly Leu Asp Leu Ser His Asn Ser
                245                 250                 255

Leu Arg Asp Ala Ala Gly Ala Pro Ser Cys Asp Trp Pro Ser Gln Leu
                260                 265                 270

Asn Ser Leu Asn Leu Ser Phe Thr Gly Leu Lys Gln Val Pro Lys Gly
        275                 280                 285

Leu Pro Ala Lys Leu Ser Val Leu Asp Leu Ser Tyr Asn Arg Leu Asp
    290                 295                 300

Arg Asn Pro Ser Pro Asp Glu Leu Pro Gln Val Gly Asn Leu Ser Leu
305                 310                 315                 320

Lys Gly Asn Pro Phe Leu Asp Ser Glu Ser His Ser Glu Lys Phe Asn
                325                 330                 335

Ser Gly Val Val Thr Ala Gly Ala Pro Ser Ser Gln Ala Val Ala Leu
            340                 345                 350

Ser Gly Thr Leu Ala Leu Leu Leu Gly Asp Arg Leu Phe Val
            355                 360                 365
```

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:7:

GCTAGCGCTA GCCACCATGG TGTGCGTGCC CTACCTGCTG    40

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:8:

GCTAGCGCTA GCCGCGAAGC CTCGGGCTCC TTGAAG                    36

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:9:

CTC GAG CTC GAG GCT AGC CAC CAT GGT GTG CGT GCC            36

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:10:

CTCGAGCTCG AGGGATCCCT AAGCGTAATC TGGAAC                    36

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:11:

TACCAATACG ATGTTCCAGA TTACGCTTAG                          30

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:12:

GCAGTCGACA CTATAGAATA CTCAAGC                            27

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:13:

TTCGTCGACA TTGGGCCCTC TAGA                                24